United States Patent
Horisberger et al.

(10) Patent No.: US 6,407,209 B1
(45) Date of Patent: Jun. 18, 2002

(54) INTERFERON-INDUCED HUMAN PROTEIN IN PURE FORM, MONOCLONAL ANTIBODIES THERETO AND TEST KITS CONTAINING THESE ANTIBODIES

(75) Inventors: Michel André Horisberger, Allschwil; Heinz-Kurt Hochkeppel, Aesch, both of (CH); Jean Content, Rhode-St-Genèse (BE)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/187,108

(22) Filed: Nov. 5, 1998

Related U.S. Application Data

(62) Division of application No. 08/941,928, filed on Oct. 1, 1997, now Pat. No. 5,869,264, which is a division of application No. 08/444,344, filed on May 18, 1995, now Pat. No. 5,739,290, which is a division of application No. 08/258,902, filed on Jun. 13, 1994, now Pat. No. 5,466,585, which is a continuation of application No. 07/983,177, filed on Nov. 30, 1992, now abandoned, which is a division of application No. 07/810,580, filed on Dec. 19, 1991, now Pat. No. 5,198,350, which is a continuation of application No. 07/497,748, filed on Mar. 19, 1990, now abandoned, which is a continuation of application No. 07/037,754, filed on Apr. 13, 1987, now abandoned.

(30) Foreign Application Priority Data

Apr. 15, 1986 (GB) ............................................. 86-09162
Oct. 23, 1986 (GB) ............................................. 86-25381

(51) Int. Cl.$^7$ .................. C07K 17/00; A61K 38/00; A61K 38/21

(52) U.S. Cl. ....................... 530/350; 514/2; 424/85.4

(58) Field of Search ............................. 530/350; 514/2; 424/85.4

(56) References Cited

U.S. PATENT DOCUMENTS 4,364,937 A  12/1982  Kung et al. ............. 530/388.75
5,391,478 A   2/1995  Greene et al. .................. 435/5

FOREIGN PATENT DOCUMENTS

WO   WO87/00864    2/1987
WO   WO8700864  *  4/1991

OTHER PUBLICATIONS

Mueller et al., 1992, J. Interferon Res. vol. 12, pp. 119–129.*
Alberts et al., 1989, Molecular Biology of the Cell, p. 162.*
Aebi et al., "cDNA Structures and Regulation of Two Interferon–Induced Human Mx Proteins", *Mol. Cell Biol.*, 9(11): 5062–5072 (1989).
Chebath et al., "Interferon–induced 56,000 Mr protein and its mRNA in human cells: molecular cloning and partial sequence of the cDNA", *Nucleic Acids Research*, 11(5): 1213–1226 (1983).
Conner et al., "Detection of sickle cell $\beta^s$ –globin allele by hybridization with synthetic oligonucleotides", *Proc. Natl. Acad. Sci. USA*, 80:278–282 (1983).
Cooper, H.L., "Effect of Bacterially Produced Interferon–$\alpha_2$ on Synthesis of Specific Peptides in Human Peripheral Lymphocytes", *FEBS Letters* 140: 109 (1982).
Gustafsson et al., "Rapid Induction of Seven Proteins in Human Lymphocytes by Interferon; Correlation to Natural Killer Cell Activity", *J. Of Immunology*, 129:19521–1959 (1982).
Horisberger et al., "IFN–$\alpha$ Induced Human 78 kD Protein: Purification and Homologies with tthe Mouse Mx Protein, Production of Monoclonal Antibodies, and Potentiation Effect of IFN–$\gamma$", *Journal of Interferon Research*, 7: 331–343 (1987).
Horisberger et al., "An Interferon–induced Mouse Protein Involved in the Mechanism of Resistance to Influenza Viruses", *J. Biol. Chem.*, 260(3): 1730–1733 (1985).
Horisberger et al., "Cloning and Sequence Analyses of cDNAs for Interferon–0 and Virus–Induced Human Mx Proteins Reveal that They Contain Putative Guanine Nucleotide–Binding Sites: Functional Study of the Corresponding Gene Promoter", *J. Virol.*, 64(3): 1171–1181 (1990).
Horisberger et al., "Cloning and Sequence Analyses of cDNAs for Interferon–and Virus Induced Human Mx Proteins Reveal that They Contain Putative Guanine Nucleotide–Binding Sites: Functional Study of the Corresponding Gene Promoter", *J. Virol.*, 64(3): 1171–1181 (1990).
Kavinsky et al., "Analysis of Cloned mRNA Sequences Encoding Subfragment 2 and Part of Subframent 1 of $\alpha$– and $\beta$– Mysoin Heavy Chains of Rabbit" *J. Biol. Chem.*, 259(5): 2775–2781 (1984).
Laurent, et al., "Monoclonal antibodies to an interferon–induced $M_r$, 68,000 protein and their use for the detection of double–stranded RNA–dependent protein kinase in human cells", *Proc. Natl. Acad. Sci. USA*, 82: 4341–4345 (1985).
Pavlovic et al., "Resistance to Influenza Virus and Vesicular Stomatitis Virus Conferred by Expression of Human MxA Protein", *J. Virol.*, 64(7): 3370–3375 (1990).

(List continued on next page.)

Primary Examiner—Yvonne Eyler
Assistant Examiner—Janet L. Andres
(74) Attorney, Agent, or Firm—Gregory D. Ferraro

(57) ABSTRACT

The invention relates to purified proteins induced in human cells by interferon $\alpha$ or $\beta$, RNAs, DNAs and hybrid vectors coding for said proteins, hosts transformed with such a hybrid vector, processes for the preparation and purification of these proteins, DNAs, vectors and hosts, monoclonal antibodies specific to these proteins, monoclonal antibody derivatives, hybridoma cell lines secreting these monoclonal antibodies, the use of the monoclonal antibodies and their derivatives in the qualitative and quantitative determination of these proteins, test kits containing the monoclonal antibodies, and pharmaceutical preparations containing said proteins. A protein of the invention shows antiviral properties ascribed to interferons and may be a valuable indicator of the cell response to an interferon therapy.

4 Claims, No Drawings

OTHER PUBLICATIONS

Staeheli et al., "Polyclonal and Monoclonal Antibodies to the Interferon–inducible Protein Mx of Influenza Virus–resistant Mice", *Journal of Biological Chemistry*, 260(3): 1821–1825 (1985).

Staeheli et al., "Interferon–Induced Human Protein with Homology to Protein Mx of Influenza Virus–Resistant Mice", *Mol. and Cellular Biology*, 5(8): 2150–2153 (1985).

Staeheli et al., "Mx Protein: Constitutive Expression in 3T3 Cells Transformed with Cloned Mx cDNA Confers Selective Resistance to Influenza Virus", *Cell*, 44: 147–158 (1986).

Staeheli et al., "Interferon–induced holologs to mouse Mx protein in humans and rats", *Biol. Interferon Syst. Proc. TNO–ISIR Meet. Interferon Syst., 4th, 1985*: 115–18 (1986).

Wallace et al., "Hybridization of synthetic oligodeoxyribonucleotides to $\Phi$ $\chi$174 DNA: the effect of single base", *Nucleic Acids Res.* 6(11): 3543–3557 (1979).

Maekawa et al, P. National Academy Science (USA) (1985) vol. 82: pp 8134–8138.

Weitz et al, J. Interferon Research (1989) vol. 9, pp 679–689.

* cited by examiner

SEQUENCE LISTING

```
<160> NUMBER OF SEQ ID NOS: 16

<210> SEQ ID NO 1
<211> LENGTH: 10
<212> TYPE: PRT
<213> ORGANISM: Homo sapiens

<400> SEQUENCE: 1

Val Val Ser Glu Val Asp Ile Ala Lys Ala
 1               5                  10

<210> SEQ ID NO 2
<211> LENGTH: 56
<212> TYPE: PRT
<213> ORGANISM: Homo sapiens

<400> SEQUENCE: 2

Val Val Ser Glu Val Asp Ile Ala Lys Ala A sp Pro Ala Ala Ala Ser
 1               5                  10                  15

His Pro Leu Leu Leu Asn Gly Asp Ala Thr V al Ala Gln Lys Asn Pro
            20                  25                  30

Gly Ser Val Ala Glu Asn Asn Leu Cys Ser G ln Tyr Glu Glu Lys Val
        35                  40                  45

Arg Pro Cys Ile Asp Leu Ile Asp
        50                  55

<210> SEQ ID NO 3
<211> LENGTH: 171
<212> TYPE: DNA
<213> ORGANISM: Homo sapiens
<220> FEATURE:
<221> NAME/KEY: CDS
<222> LOCATION: (1)..(171)

<400> SEQUENCE: 3
```

```
atg gtt gtt tcc gaa gtg gac atc gca aaa g ct gat cca gct gct gca        48
Met Val Val Ser Glu Val Asp Ile Ala Lys A la Asp Pro Ala Ala Ala
 1               5                   10                  15 tcc cac cct cta tta ctg aat gga gat gct a ct gtg gcc cag aaa aat        96
Ser His Pro Leu Leu Leu Asn Gly Asp Ala T hr Val Ala Gln Lys Asn
                20                  25                  30 cca ggc tcg gtg gct gag aac aac ctg tgc a gc cag tat gag gag aag       144
Pro Gly Ser Val Ala Glu Asn Asn Leu Cys S er Gln Tyr Glu Glu Lys
         35                  40                  45 gtg cgc ccc tgc atc gac ctc att gac                                    171
Val Arg Pro Cys Ile Asp Leu Ile Asp
         50                  55

<210> SEQ ID NO 4
<211> LENGTH: 57
<212> TYPE: PRT
<213> ORGANISM: Homo sapiens

<400> SEQUENCE: 4

Met Val Val Ser Glu Val Asp Ile Ala Lys A la Asp Pro Ala Ala Ala
 1               5                   10                  15

Ser His Pro Leu Leu Leu Asn Gly Asp Ala T hr Val Ala Gln Lys Asn
                20                  25                  30

Pro Gly Ser Val Ala Glu Asn Asn Leu Cys S er Gln Tyr Glu Glu Lys
         35                  40                  45

Val Arg Pro Cys Ile Asp Leu Ile Asp
         50                  55

<210> SEQ ID NO 5
<211> LENGTH: 253
<212> TYPE: DNA
<213> ORGANISM: Homo sapiens
<220> FEATURE:
<221> NAME/KEY: CDS
<222> LOCATION: (83)..(253)

<400> SEQUENCE: 5
agctctgtga taccatttaa cttgttgaca ttacttttat ttgaaggaac g tatattaga     60 gcttactttg caaagaagga ag atg gtt gtt tcc gaa gt g gac atc gca aaa    112
                         Met Val Val Ser Glu Val A sp Ile Ala Lys
                          1               5                   10 gct gat cca gct gct gca tcc cac cct cta t ta ctg aat gga gat gct     160
Ala Asp Pro Ala Ala Ala Ser His Pro Leu L eu Leu Asn Gly Asp Ala
             15                  20                  25 act gtg gcc cag aaa aat cca ggc tcg gtg g ct gag aac aac ctg tgc     208
Thr Val Ala Gln Lys Asn Pro Gly Ser Val A la Glu Asn Asn Leu Cys
         30                  35                  40 agc cag tat gag gag aag gtg cgc ccc tgc a tc gac ctc att gac         2 53
Ser Gln Tyr Glu Glu Lys Val Arg Pro Cys I le Asp Leu Ile Asp
         45                  50                  55

<210> SEQ ID NO 6
<211> LENGTH: 57
<212> TYPE: PRT
<213> ORGANISM: Homo sapiens

<400> SEQUENCE: 6

Met Val Val Ser Glu Val Asp Ile Ala Lys A la Asp Pro Ala Ala Ala
 1               5                   10                  15

Ser His Pro Leu Leu Leu Asn Gly Asp Ala T hr Val Ala Gln Lys Asn
                20                  25                  30
```

```
Pro Gly Ser Val Ala Glu Asn Asn Leu Cys S er Gln Tyr Glu Glu Lys
         35                  40                    45

Val Arg Pro Cys Ile Asp Leu Ile Asp
         50                  55

<210> SEQ ID NO 7
<211> LENGTH: 641
<212> TYPE: DNA
<213> ORGANISM: Homo sapiens
<220> FEATURE:
<221> NAME/KEY: CDS
<222> LOCATION: (268)..(639)
<220> FEATURE:
<221> NAME/KEY: misc_feature
<222> LOCATION: (30,53)..(60)
<223> OTHER INFORMATION: n can be A or C or G or T/U

<400> SEQUENCE: 7
tggacacgcc tccctcgcgc ccttgccgcn cacctgctca cccagctcag g gnctttgga      60 attctntggc cacactgcga ggagatcggt tctgggtcgg aggctacagg a agactccca    120 ctccctgaaa tctggagtga agaacgccgc catccagcca ccattccaag g aggtgcagg    180 agaacagctc tgtgatacca tttaacttgt tgacattact tttatttgaa g gaacgtata    240 ttagagctta ctttgcaaag aaggaag atg gtt gtt tcc gaa gtg gac atc gca    294
                               Met Val Val Se r Glu Val Asp Ile Ala
                                 1                  5
```

```
aaa gct gat cca gct gct gca tcc cac cct c ta tta ctg aat gga gat    342
Lys Ala Asp Pro Ala Ala Ala Ser His Pro L eu Leu Leu Asn Gly Asp
 10                  15                  20                  25 gct act gtg gcc cag aaa aat cca ggc tcg g tg gct gag aac aac ctg    390
Ala Thr Val Ala Gln Lys Asn Pro Gly Ser V al Ala Glu Asn Asn Leu
                 30                  35                      40 tgc agc cag tat gag gag aag gtg cgc ccc t gc atc gac ctc att gac    438
Cys Ser Gln Tyr Glu Glu Lys Val Arg Pro C ys Ile Asp Leu Ile Asp
             45                  50                  55 tcc ctg cgg gct cta ggt gtg gag cag gac c tg gcc ctg cca gcc atc    486
Ser Leu Arg Ala Leu Gly Val Glu Gln Asp L eu Ala Leu Pro Ala Ile
         60                  65                  70 gcc gtc atc ggg gac cag agc tcg ggc aag a gc tcc gtg ttg gag gca    534
Ala Val Ile Gly Asp Gln Ser Ser Gly Lys S er Ser Val Leu Glu Ala
     75                  80                  85 ctg tca gga gtt gcc ctt ccc aga ggc agc g gg atc gtg acc aga tgc    582
Leu Ser Gly Val Ala Leu Pro Arg Gly Ser G ly Ile Val Thr Arg Cys
 90                  95                  100                 105 ccg ctg gtg ctg aaa ctg aag aaa ctt gtg a ac gaa gat aag tgg aga    630
Pro Leu Val Leu Lys Leu Lys Lys Leu Val A sn Glu Asp Lys Trp Arg
                 110                 115                 120 ggc aag gtc ag                                                       641
Gly Lys Val <210> SEQ ID NO 8
<211> LENGTH: 124
<212> TYPE: PRT
<213> ORGANISM: Homo sapiens

<400> SEQUENCE: 8

Met Val Val Ser Glu Val Asp Ile Ala Lys A la Asp Pro Ala Ala Ala
  1               5                  10                  15

Ser His Pro Leu Leu Leu Asn Gly Asp Ala T hr Val Ala Gln Lys Asn
             20                  25                  30
```

Pro Gly Ser Val Ala Glu Asn Asn Leu Cys Ser Gln Tyr Glu Glu Lys
          35                  40                  45

Val Arg Pro Cys Ile Asp Leu Ile Asp Ser Leu Arg Ala Leu Gly Val
     50                  55                  60

Glu Gln Asp Leu Ala Leu Pro Ala Ile Ala Val Ile Gly Asp Gln Ser
 65                  70                  75                  80

Ser Gly Lys Ser Ser Val Leu Glu Ala Leu Ser Gly Val Ala Leu Pro
                 85                  90                  95

Arg Gly Ser Gly Ile Val Thr Arg Cys Pro Leu Val Leu Lys Leu Lys
                100                 105                 110

Lys Leu Val Asn Glu Asp Lys Trp Arg Gly Lys Val
         115                 120

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
gcttttgcga tgtccacttc                                              20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
cagccaccat tccaagg                                                 17

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
cgcaccttct cctcatactg g                                            21

<210> SEQ ID NO 12
<211> LENGTH: 13
<212> TYPE: PRT
<213> ORGANISM: Homo sapiens
<220> FEATURE:
<221> NAME/KEY: UNSURE
<222> LOCATION: (3)
<223> OTHER INFORMATION: Third amino acid could not be identified

<400> SEQUENCE: 12

Val Val Xaa Glu Val Asp Ile Ala Lys Ala Pro Lys Ala
  1               5                  10

<210> SEQ ID NO 13
<211> LENGTH: 7
<212> TYPE: PRT
<213> ORGANISM: Homo sapiens

<400> SEQUENCE: 13

```
Glu Val Asp Ile Ala Lys Ala
 1               5
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: modified_base
<222> LOCATION: (6)..(15)
<223> OTHER INFORMATION: N stands for Inosine

<400> SEQUENCE: 14
gcyttngcda trtcnacytc                                              20

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
cagccaccat tccaagg                                                 17

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
cgcaccttct cctcatactg g                                            21

INTERFERON-INDUCED HUMAN PROTEIN IN PURE FORM, MONOCLONAL ANTIBODIES THERETO AND TEST KITS CONTAINING THESE ANTIBODIES

This application is a divisional application of pending U.S. application Ser. No. 08/941,928 filed Oct. 1, 1997, now U.S. Pat. No. 5,869,264 which is a divisional of Ser. No. 08/444,344 filed May 18, 1995, now U.S. Pat. No. 5,739,290, which is a divisional of Ser. No. 08/1258,902, filed Jun. 13, 1994, now U.S. Pat. No. 5,466,585 which is a Continuation of Ser. No. 07/983,177, filed Nov. 30, 1992, now abandoned which is a divisional of Ser. No. 07/810,580, filed Dec. 19, 1991 now U.S. Pat. No. 5,198,350 which is a Continuation of Ser. No. 07/497,748, filed Mar. 19, 1990, now abandoned, which is a Continuation of Ser. No. 07/037,754, filed Apr. 13, 1987, now abandoned.

FIELD OF THE INVENTION

The invention relates to purified proteins induced in human cells by interferon $\alpha$ or $\beta$, RNAs, DNAs and hybrid vectors coding for said proteins, hosts transformed with such a hybrid vector, processes for the preparation and purification of these proteins, DNAs, vectors and hosts, monoclonal antibodies specific to these proteins, monoclonal antibody derivatives, hybridoma cell lines secreting these monoclonal antibodies, the use of the monoclonal antibodies and their derivatives in the qualitative and quantitative determination of these proteins, test kits containing the monoclonal antibodies, and pharmaceutical preparations containing said proteins.

BACKGROUND OF THE INVENTION

Interferons are a class of naturally occurring proteins which show promise in the defense against viral infections and in tumor growth control. They seem to interfere with cellular functions necessary for viral replication and to inhibit cellular growth by pleiotropic effects which are not yet understood at the molecular level. Furthermore, interferons stimulate the activity of natural killer (NK) cells, and within a complicated network of lymphokine interactions, modulate the activity of macrophages, B- and T-cells.

A set of induced proteins may be involved in the antiviral, antiproliferative and immunomodulatory activities of interferons. In mammalian cells interferons induce the synthesis of several proteins that are not detected or do exist at much lower concentrations in untreated cells. Some of these induced proteins have been widely studied [review: P. Lengyel, Annu. Rev. Biochem. 51, 251 (1982)], but are still poorly characterized. Interferon-treated cells of both human and mouse origin contain elevated levels of 2',5'-oligoisoadenylate synthetase and protein kinase activities. The synthesis and properties of the mouse protein Mx induced by interferon $\alpha$ and $\beta$ have been studied in detail [P. Staeheli et al., Cell 44, 147 (1986)]. This protein is associated with a highly efficient and specific antiviral resistance to influenza viruses [M. A. Horisberger et al., Proc. Natl. Acad. Sci. USA 80, 1910 (1983); M. A. Horisberger & H. K. Hochkeppel, J. Biol. Chem. 260, 1730 (1985)]. A related human protein was detected in interferon-induced human peripheral blood lymphocytes and fibroblasts [P. Staeheli & O. Haller, Mol. Cell. Biol. 5, 2150 (1985)]. A molecular weight of 80 kDa (kilo-Dalton) was found, and the protein was predominantly localized in the cell cytoplasm, but otherwise the protein was not further characterized or isolated.

The fast progress in recombinant DNA technology in recent years provides the general methods for the preparation of proteins in large amounts independent of the primary natural sources of such compounds. Identification of an mRNA or a DNA coding for the desired polypeptide is crucial for the success of this approach. If (partial) amino acid sequence information is available, a chemically synthetized nucleic acid probe may lead to the isolation of coding mRNA or DNA from a mixture of mRNA derived from cells producing the desired polypeptides or from a DNA library, respectively. Although many examples for the isolation of an mRNA or DNA coding for a desired polypeptide have so far become known and the general procedure has been described in principle, each new specific problem requires adaption of the technique to the particular case.

Once a complementary or genomic DNA coding for the desired polypeptide is at hand, preparation of suitable expression vectors, transformation of hosts with these vectors, fermentation of transformed hosts and isolation of the expressed polypeptide follows standard procedures. Here again, these procedures must be adapted to the particular problem in order to get stable incorporation of the DNA and sufficiently high expression of the desired polypeptide in a chosen host organism, and acceptable yields of pure, biologically active isolated protein.

Furthermore recombinant DNA technology allows one to produce polypeptide variants by mutating or otherwise altering the coding DNA incorporated in a host organism, thereby enlarging the potential applications of an active principle found in a single polypeptide structure in nature.

Proteins induced by interferon are important in diagnosis, disease management and therapy in two respects: On one hand they may exert some of the beneficial properties such as antiviral or antiproliferative activities ascribed to interferons, but without the unwanted side effects of interferons, on the other hand they may be valuable indicators of the cell response to an interferon therapy. Antibodies to such interferon-induced proteins allow the qualitative and quantitative determination of these proteins and therefore are indispensable means in the surveillance of a therapy with these proteins or with interferons.

Polyclonal and monoclonal antibodies to the mouse Mx protein induced by interferons are known [P. Staeheli & O. Haller, Mol. Cell. Biol. 5, 2150 (1985)]. One of these shows also a weak cross-reactivity to a human interferon-induced protein, however, non-specific cross-reaction cannot be excluded.

OBJECT OF THE INVENTION

It is an object of the present invention to provide pure proteins related to or identical with those found in human cells induced by interferon $\alpha$ or $\beta$. The problem of industrial synthesis of such proteins can be solved by the methods of recombinant DNA technology. A further object of the present invention is therefore to provide mRNAs, DNAs and hybrid vectors coding for said proteins, and hosts transformed with such a vector.

Further objects are processes for the preparation and purification of said proteins, mRNAs, DNAs and hybrid vectors, and processes for tie preparation of hosts containing said hybrid vectors.

It is another object of the invention to provide monoclonal antibodies as diagnostic means for the qualitative and quantitative determination of said proteins, hybridomas secreting such antibodies, and processes for the preparation of these antibodies and hybridomas, furthermore pharmaceutical preparations containing said proteins.

DESCRIPTION OF THE INVENTION

The invention relates to essentially pure proteins, characterized by (1) their presence in human cells induced by interferon $\alpha$ or $\beta$, but not in untreated cells to a reasonable extent, (2) a molecular weight of approximately 78 kDa as determined by sodium dodecyl sulfate polyacrylamide gel electrophotesis (SDS-PAGE), (3) an isoelectric point of approximately 6.3, (4) a partial N-terminal amino acid sequence

```
                                        (SEQ ID NO.1)
             5                  10
Val-Val-Ser-Glu-Val-Asp-Ile-Ala-Lys-Ala-.
```

In particular, these proteins are found in Namalwa or human embryonic foreskin cells treated with a recombinant interferon α/B, α/D, α/F or interferon α/B–D hybrids.

Particularly preferred is a protein with a partial N-terminal amino acid sequence

```
             5                  10                15        (SEQ ID NO.2)
Val-Val-Ser-Glu-Val-Asp-Ile-Ala-Lys-Ala-Asp-Pro-Ala-Ala-Ala-Ser- 20                  25                30
His-Pro-Leu-Leu-Leu-Asn-Gly-Asp-Ala-Thr-Val-Ala-Gln-Lys-Asn-Pro- 35                  40                45
Gly-Ser-Val-Ala-Glu-Asn-Asn-Leu-Cys-Ser-Gln-Tyr-Glu-Glu-Lys-Val- 50                  55
Arg-Pro-Gys-Ile-Asp-Leu-Ile-Asp-.
```

The molecular weight of 78 kDa is based on SDS-PAGE with the usual molecular weight markers. However, it can be inferred from work with the related mouse protein Mx [P. Staeheli et al., Cell 44, 147 (1986))] that the actual molecular weight is lower, probably around 72 kDa.

The proteins are further characterized by the amino acid composition as determined by a total amino acid analysis based on a molecular weight of 72 kDa (Table 1). The range of actual number of amino acids of the analyzed proteins given in Table 1 is calculated from the uncertainty (standard deviation) of the method of analysis.

TABLE 1

Amino acid composition

| amino acid | amount determined | actual number of amino acids (range) |
|---|---|---|
| Asx (Aspartic acid/Asparagine) | 56.8 | 54–60 |
| Glx (Glutamic acid/Glutamine) | 96.1 | 91–101 |
| Ser (Serine) | 39.3 | 37–41 |
| Thr (Threonine) | 32.2 | 30–34 |
| Gly (Glycine) | 43.4 | 41–46 |
| Ala (Alanine) | 47.2 | 45–50 |
| Arg (Arginine) | 38.2 | 36–40 |
| Pro (Proline) | 26.0 | 24–28 |
| Val (Valine) | 39.9 | 38–42 |
| Met (Methionine) | 18.0 | 17–19 |
| Ile (Isoleucine) | 43.1 | 41–46 |
| Leu (Leucine) | 68.1 | 64–72 |
| Trp (Tryptophan) | 0 | 0–3 |
| Phe (Phenylalanine) | 25.4 | 24–27 |
| Cys (Cysteine) | 5.9 | 5–7 |
| Lys (Lysine) | 47.5 | 45–50 |
| His (Histidine) | 12.9 | 12–14 |
| Tyr (Tyrosine) | 11.8 | 11–13 |

The invention relates also to a process for the preparation of such a protein, characterized in that cells producing said protein are cultured and the protein is isolated from the cell supernatant or cell lysis mixture and purified by precipitation and chromatographic methods.

In particular, the invention relates to a process for the preparation of such a protein in purified form, characterized in that human cells, preferably cells of a continous human cell line, e.g. Namalwa cells or embryonic foreskin cells, are cultured in the presence of human interferon α or β, e.g. natural human interferon α or recombinant human interferon α, such as interferon α/B, α/D, α/F or α/B–D hybrids, the cells are lysed, the proteins in the supernatants are precipitated, e.g. by addition of ammonium sulfate, then separated by preparative gel electrophoresis, and the protein of an apparent molecular weight of approximately 78 kDa is eluted, e.g. by electrodialysis.

Human cells useful for the preparation of the proteins of the invention are normal lymphocytes, macrophages or monocytes, lymphoblastoid cells, e.g. Namalwa cells, or human embryonic foreskin cells from a diploid cell line.

Preferably, Namalwa cells are cultured in the usual cell growth media, e.g. RPMI 1640 medium supplemented with vitamins and/or hormones, for example in the form of fetal calf serum, and optionally antibiotics. At the end of exponential growth, the cells are incubated with recombinant interferon a, e.g. α/B subtype or α/B–D hybrids, in concentrations ranging from $5 \times 10^5$ to $10^7$ cells per ml and 2000 to 10,000 international interferon units per ml, preferably around 37° C.

Any of the known natural or recombinant interferon α or β may be used to induce the production of the proteins of the invention, e.g. the recombinant interferons described in the patent applications EP 28 033, EP 32 134, EP 43 908, EP 72 541 or EP 76 489.

The cells are harvested and lysed by the usual methods, e.g. by high salt concentrations in buffered solution, and the protein precipitated, e.g. by addition of ammonium sulfate. The desired protein is rather insoluble in the usual physiological solvent systems.

The desired protein is purified by gel electrophoresis. Preferably the preparative gel electrophoresis is performed twice, e.g. first to effect crude separation from proteins with molecular weight less than 70 kDa and more than 85 kDa, then by two-dimensional separation of the resulting protein mixture, combining non-equilibrium pH gradient electrophoresis with SDS-polyacrylamide gel electrophoresis. In particular, the protein mixture is applied to the acidic end of the non-equilibrium pH gradient electrophoresis gel, which contains 2% ampholytes, pH 3–10, separated electrophoretically, then separated in the second dimension on a slab gel containing 10–15%, preferably 12%, acrylamide and up to 0.5%, e.g. around 0.3%, bis-acrylamide.

Preferably, a protein of the invention is prepared by recombinant DNA technique comprising, for example, culturing a transformed host expressing the protein as defined hereinbefore under conditions which allow expression of the heterologous polypeptide and isolating the desired compound. More specifically, the desired protein is prepared by a) isolating a DNA coding for the protein from a cDNA or a genomic DNA library of human cells, b) incorporating the DNA into an appropriate expression vector, c) transferring the obtained hybrid vector into a recipient host, d) selecting the transformed host from untransformed hosts, e.g. by culturing under conditions under which only the transformed host survives, e) culturing the transformed host under conditions which allow expression of the heterologous polypeptide, and f) isolating the desired protein.

The steps involved in the preparation of these peptides by recombinant DNA technique will be discussed in more detail hereinbelow.

The invention relates also to DNAs coding for proteins as described hereinbefore. In particular the invention concerns a DNA of the formula

```
        1                              10                                      (I), (SEQ ID NO.3 and 4)
    MetValValSerGluValAspIleAlaLysAlaAspProAlaAlaAlaSerHisProLeu
Z¹-ATGGTTGTTTCCGAAGTGGACATCGCAAAAGCTGATCCAGCTGCTGCATCCCACCCTCTA
    1        10        20        30        40        50        60

20                             30
    LeuLeuAsnGlyAspAlaThrValAlaGlnLysAsnProGlySerValAlaGluAsnAsn
    TTACTGAATGGAGATGCTACTGTGGCCCAGAAAAATCCAGGCTCGGTGGCTGAGAACAAC
            70        80        90       100       110       120

40                          50
    LeuCysSerGlnTyrGluGluLysValArgProCysIleAspLeuIleAsp
    CTGTGCAGCCAGTATGAGGAGAAGGTGCGCCCCTGCATCGACCTCATTGAC-Z²
           130       140       150       160       170
``` wherein $Z^1$ is a 5'-end DNA residue of 12 nucleotides or more containing a promoter sequence, $Z^2$ is a DNA residue of 1700 or more coding nucleotides, a stop codon and optionally non-coding nucleotides at the 3'-end, and $Z^1$ and $Z^2$ are optionally linked,
a DNA of formula I wherein one or more triplet codons are replaced by other triplet codons for the same amino acids, a double-stranded DNA consisting of a DNA of formula I and of a complementary DNA thereto, and that complementary DNA itself.

An example of a DNA of the formula I is e.g. the cDNA which is derived from the mRNA of a human embryonic foreskin cell, of the formula

```
Z³-AGGTCTGTGATACCATTTAACTTGTTGACATTACTTTTATTTGAAGGAACGTATATTA     (II), (SEQ ID NO.5 and 6)
    -80       -70       -60       -50       -40       -30

1                        10
                              MetValValSerGluValAspIleAlaLysAlaAsp
    GAGCTTACTTTGCAAAGAAGGAAGATGGTTGTTTCCGAAGTGGACATCGCAAAAGCTGAT
       -20       -10        1        10        20        30

20                              30
    ProAlaAlaAlaSerHisProLeuLeuLeuAsnGlyAspAlaThrValAlaGlnLysAsn
    CCAGCTGCTGCATCCCACCCTCTATTACTGAATGGAGATGCTACTGTGGCCCAGAAAAAT
       40        50        60        70        80        90

40                             50
    ProGlySerValAlaGluAsnAsnLeuCysSerGlnTyrGluGluLysValArgProCys
    CCAGGCTCGGTGGCTGAGAACAACCTGTGCAGCCAGTATGAGGAGAAGGTGCGCCCCTGC
       100       110       120       130       140       150

IleAspLeuIleAsp
    ATCGACCTCATTGAC-Z²
       160       170
``` wherein $Z^3$ is a 5'-end DNA residue of one or more nucleotides and $Z^2$ has the meaning given under formula I, in particular the cDNA of the formula

```
Z⁴-TGGACACGCCTCCCTCGCGCCCTTGCCGCXCACCTGCTCACCCAGCTCAGGGXCTTTGGA    (III), (SEQ ID NO. 7 and 8)
     -270      -260      -250      -240      -230      -220

ATTCTXTGGCCACACTGCGAGGAGATCGGTTCTGGGTCGGAGGCTACAGGAAGACTCCCA
     -200      -190      -180      -170      -160      -150

CTCCCTGAAATCTGGAGTGAAGAACGCCGCCATCCAGCCACCATTCCAAGGAGGTGCAGG
     -140      -130      -120      -110      -100      -90

AGAACAGCTCTGTGATACCATTTAACTTGTTGACATTACTTTTATTTGAAGGAACGTATA
      -80       -70       -60       -50       -40       -30

1                         10
                                    MetValValSerGluValAspIleAlaLysAla
    TTAGACCTTACTTTGCAAAGAAGGAAGATGGTTGTTTCCGAAGTGGACATCGCAAAAGCT
      -20       -10        1        10        20        30

20                         30
    AspProAlaAlaAlaSerHisProLeuLeuLeuAsnGlyAspAlaThrValAlaGlnLys
    GATCCAGCTGCTGCATCCCACCCTCTATTACTGAATGGAGATGCTACTGTGGCCCAGAAA
       40        50        60        70        80        90

40                         50
    AsnProGlySerValAlaGluAsnAsnLeuCysSerGlnTyrGluGluLysValArgPro
    AATCCAGGCTCGGTGGCTGAGAACAACCTGTGCAGCCAGTATGAGGAGAAGGTGCGCCCC
      100       110       120       130       140       150

60                         70
    CysIleAspLeuIleAspSerLeuArgAlaLeuGlyValGluGlnAspLeuAlaLeuPro
    TGCATCGACCTCATTGACTCCCTGCGGGCTCTAGGTGTGGAGCAGGACCTGGCCCTGCCA
      160       170       180       190       200       210

80                         90
    AlaIleAlaValIleGlyAspGlnSerSerGlyLysSerSerValLeuGluAlaLeuSer
    GCCATCGCCGTCATCGGGGACCAGAGCTCGGGCAAGAGCTCCGTGTTGGAGGCACTGTCA
      220       230       240       250       260       270

100                        110
    GlyValAlaLeuProArgGlySerGlyIleValThrArgCysProLeuValLeuLysLeu
    GGAGTTGCCCTTCCCAGAGGCAGCGGGATCGTGACCAGATGCCCGCTGGTGCTGAAACTG
      280       290       300       310       320       330

120
    LysLysLeuValAsnGluAspLysTrpArgGlyLysVal
    AAGAAACTTGTGAACGAAGATAAGTGGAGAGGCAAGGTCAG-Z⁵
      340       350       360       370
``` wherein $Z^4$ is a 5'-end DNA residue of one or more nucleotides and $Z^5$ is a DNA residue of 1500 or more coding nucleotides, a stop codon and optionally non-coding nucleotides at the 3'-end.

Furthermore, the invention relates also to a DNA which hybridizes with a DNA of formula I, II or III, e.g. the 20-mer oligonucleotide of the formula

5'-GCTTTTGCGATGTCCACTTC-3'    (IV), (SEQ ID NO.9)

the 17-mer oligonucleotide of the formula

5'-CAGCCACCATTCCAAGG-3'    (V), (SEQ ID NO.10)

and the 21-mer oligonucleotide of the formula

5'-CGCACCTTCTCCTCATACTGG-3'    (VI), (SEQ ID NO.11)

The invention relates also to an RNA coding for proteins as described hereinbefore, in particular to an RNA of the formula I, II or III, wherein $Z^1$ to $Z^5$ have the meanings given hereinbefore except that RNA residues replace DNA residues and hence uridine (U) replaces deoxy-thymidine (T).

The DNAs coding for the desired proteins can be prepared, for example, by culturing a transformed host and isolating the desired DNA therefrom.

In particular, such DNAs can be prepared by
a) isolating mRNA from human cells, selecting the desired mRNA, preparing single-stranded DNA complementary to that mRNA, then double-stranded DNA (ds cDNA) therefrom, or
b) isolating genomic DNA from human cells and selecting the desired DNA using a DNA probe, and
c) incorporating ds cDNA of step a) or ds DNA of step b) into an appropriate expression vector,
d) transforming an appropriate host microorganism with the obtained hybrid vector,
e) selecting the transformed host which contains DNA coding for the desired protein from hosts containing no coding DNA, and
f) isolating the desired DNA.

Polyadenylated messenger RNA is isolated from human cells by known methods. Suitable cells are normal lymphocytes, macrophages, monocytes, lymphoblastoid cells, e.g. Namalwa cells, human embryonic foreskin diploid cells or the like, induced with natural or recombinant interferon α or β. Isolation methods involve, for example, lysing stimulated cells in the presence of a detergent and optionally a ribonuclease inhibitor, e.g. heparin, guanidinium isothiocyanate and mercaptoethanol, extracting the mRNA with phenol or suitable chloroform-phenol mixtures, optionally in the presence of salt and buffer solutions, detergents, proteinase and/or cation chelating agents, and precipitating mRNA from the remaining aqueous, salt-containing phase with ethanol, isopropanol or the like. The isolated mRNA may be further purified by centrifuging in a cesium chloride gradient followed by ethanol precipitation and/or by chromatographic methods, e.g. affinity chromatography, for example chromatography on oligo(dT) cellulose or on oligo (U) sepharose. Preferably, crude or purified total mRNA is fractionated according to size by gradient centrifugation, e.g. in a linear sucrose gradient, or chromatography on suitable size fractionation columns, e.g. on agarose gels.

The desired mRNA is selected by screening with a DNA probe or by translation in suitable cells or cell-free system and screening the obtained polypeptides. Preferably, fractionated mRNA is translated in cells, e.g. in frog oocytes, or in cell-free systems, e.g. in reticulocyte lysates or wheat germ extracts. The obtained polypeptides are compared with native protein purified as described hereinbefore, e.g. by polyacrylamide gel electrophoresis, and mRNA fractions giving rise to the desired protein selected.

The preparation of a single-stranded complementary DNA from the selected mRNA template is well known in the art, as is the preparation of a double-stranded DNA from a single-stranded DNA. The mRNA template is incubated with a mix of deoxynucleotide triphosphates, optionally a radioactively labelled deoxynucleotide triphosphate (in order to be able to screen the result of the reaction), a primer sequence such as an oligo(dT) residue hybridizing with the poly(A) tail of the messenger RNA and a suitable enzyme, e.g. a reverse transcriptase. After degradation of the template mRNA, the complementary DNA (cDNA) is incubated with a mix of deoxynucleotide triphosphates and a suitable enzyme as above to give a double-stranded DNA. Suitable enzymes are a reverse transcriptase, the Klenow fragment of $E.$ $coli$ DNA polymerase I or $T_4$ DNA polymerase. Optionally, the single-stranded DNA is first extended with a tail of like deoxynucleotides to allow the use of a primer sequence of complementary like deoxynucleotides, but the formation of dsDNA usually starts on spontaneous hairpin formation. Such dsDNA obtained as a result of hairpin formation is further processed with SI nuclease which cuts the hairpin. In a preferred alternative protocol, the mRNA/DNA hybrid is treated directly with RNase H, $T_4$ DNA ligase and DNA polymerase I, thus avoiding the additional steps of extending with a primer sequence and/or hairpin cutting.

As an alternative to the preparation of cDNA from mRNA, genomic DNA may be isolated and screened for DNA coding for the desired polypeptide.

Genomic DNA is isolated from suitable human tissue, preferably from human placenta or human fetal liver cells, according to methods known in the art. A genomic DNA library is prepared therefrom by digestion with suitable restriction endonucleases and incorporation into λ charon phage, e.g. λ charon 4A, following established procedures. The genomic DNA library replicated on nitrocellulose membranes is screened with a DNA probe, e.g. a synthetic DNA probe of at least 17 nucleotides or a cDNA derived from mRNA coding for the desired polypeptide, as described hereinbefore.

The incorporation of dsDNA prepared from mRNA or of genomic origin into an appropriate vector is well known in the art. For example, a suitable vector is cut and provided with tails of like deoxynucleotides. The dsDNA to be annealed then has to bear tails of complementary like deoxynucleotides, which is accomplished by incubation in the presence of the corresponding deoxynucleotide triphosphate and an enzyme such as terminal deoxynucleotidyl transferase. Otherwise, the dsDNA may be incorporated into the vector by simple ligation after treatment with the same endonuclease yielding complementary protruding ends, with the aid of linker oligonucleotides or else by blunt end ligation.

The transformation of an appropriate host microorganism with the obtained hybrid vector is well known in the art. For example, $E.$ $coli$ are conditioned for transformation by incubation in media containing calcium chloride, then treated with the hybrid vector. Transformed hosts are selected by suitable markers, for example by an antibiotics resistance marker, e.g. tetracycline, chloramphenicol or ampicillin resistance, and/or by an enzyme marker, e.g. β-galactosidase complementing α-protein.

Hosts transformed with the desired DNA are preferably selected using a DNA probe. Such hybridization probe is e.g. a fully synthetic DNA consisting of at least 17 nucleotides, e.g. around 20 nucleotides, constructed on the basis of the partial amino acid sequence determined on the desired protein isolated from interferon-induced Namalwa cells. Preferably mixtures of oligonucleotide probes are prepared, wherein each member of the mixture is complementary to one of the possible combinations of triplet codons for the corresponding known amino acid sequence.

Such DNA probes are also comprised by the present invention. They are synthesized according to known methods, preferably by stepwise condensation using the solid phase phosphotriester, phosphite triester or phosphoramidite method, e.g. the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. Ike et al. [Nucleic Acid Research 11, 477 (1983)].

The DNA probes have to contain a marker so that hybridization with DNA of transformed hosts can be detected and the hosts identified and separated from other hosts not containing the desired DNA of the present invention. Suitable are e.g. radioactive labels such as $^{32}P$ in the 5'-end phosphate of the oligonucleotide, or fluorescent markers or a label containing biotin which can be detected with suitably labelled avidin, e.g. avidin bearing a fluorescent marker or conjugated with an enzyme such as horseradish peroxidase.

Hybridization of DNA from transformed hosts with the DNA probes containing a marker is performed according to known procedures, i.e. in buffer and salt solutions containing adjuncts, e.g. calcium chelators, viscosity regulating compounds, proteins, irrelevant DNA or tRNA and the like, at temperatures favoring selective hybridization, e.g. between 0° and 70° C., for example between 40 and 50° C., preferably at around 20° lower than the hybrid dsDNA melting temperature.

The invention further relates to hybrid vectors comprising a DNA coding for the desired proteins operatively linked to an expression control sequence, and to processes for the preparation thereof. The vector is selected depending on the host cells envisaged for transformation. Examples of suitable hosts are microorganisms, which are devoid of or poor in restriction enzymes or modification enzymes, such as yeasts, for example $Saccharomyces$ $cerevisiae,$ for example $S.$ $cerevisiae$ GRF 18, and strains of bacteria, in particular strains of $Escherichia$ $coli,$ for example $E.$ $coli$ X1776, $E.$ $coli$ HB 101, $E.$ $coli$ W3110, $E.$ $coli$ HB101/LM1035, $E.$ $coli$ JA221, $E.$ $coli$ JM109 or $E.$ $coli$ K12 strain 294, $Bacillus$ $subtilis,$ $Bacillus$ $stearothermophilus,$ Pseudomonas, Haemophilus, Streptococcus and others, and furthermore cells of higher organisms, in particular established human or animal cell lines, e.g. Hela cells, SV-40 virus transformed kidney cells of African green monkey COS-7 or chinese hamster ovary (CHO) cells. The above strains of E. coli, for example E. coli JM 109, E. coli HB101, E. coli K12 and E. coli W3110, and of Saccharomyces cerevisiae are preferred as the host microorganism. In principle, all vectors which replicate and express the desired polypeptide gene according to the invention in the chosen host are suitable. Examples of vectors which are suitable for the expression in an E. coli strain are bacteriophages, for example derivatives of lambda or M13 bacteriophages, or plasmids, such as, in particular, the plasmid ColEl and its derivatives, for example pMB9, pSF2124, pBR317 or pBR322. The preferred vectors of the present invention are derived from plasmid pBR322. Suitable vectors contain a complete replicon and a marker gene, which allows to select and identify the hosts transformed with the expression plasmids on the basis of a phenotypical trait, and optionally signal sequences and enhancers. Suitable marker genes impart to the host, for example, resistance towards heavy metals, antibiotics and the like. Furthermore, preferred vectors of the present invention contain, outside the replicon and marker gene regions, recognition sequences for restriction endonucleases, so that the gene for the desired peptide and, if appropriate, the expression control sequence can be inserted at these sites. The preferred vector, the plasmid pBR322 and derived plasmids, e.g. pUC9, pHRil48 and pPLc24, contain an intact replicon, marker genes, which confer resistance e.g. towards. tetracycline and ampicillin ($tet^R$ and $amp^R$), and a number of unique recognition sites for restriction endonucleases.

Several expression control sequences can be used for regulation of the gene expression. In particular, expression control sequences of highly expressed genes of the host to be transformed are used. In the case of pBR322 as the hybrid vector and E. coli as the host microorganism, for example, the expression control sequences (which contain, inter alia, the promoter and the ribosomal binding site) of the lactose operon, tryptophan operon, arabinose operon and the like, the β-lactamase gene, the corresponding sequences of the phage λ N gene, especially those containing the $P_L$ promoter, or the phage fd-coat protein gene and others are suitable. Whilst the plasmid pBR322 already contains the promoter of the β-lactamase gene (β-lac gene), the other expression control sequences must be introduced into the plasmid.

Vectors which are suitable for replication and expression in yeast contain a yeast replication start and a selective genetic marker for yeast. Hybrid vectors which contain a yeast replication start, for example chromosomal autonomously replicating segment (ars), are retained extrachromosomally within the yeast cell after the transformation and are replicated autonomously. Furthermore, hybrid vectors which contain sequences homologous to the yeast 2μ plasmid DNA can be used. Such hybrid vectors will get integrated by recombination into 2μ plasmids already existing within the cell, or replicate autonomously. 2μ sequences are particularly suitable for plasmids with a high transformation frequency and permit high copy numbers. The preferred yeast vector of the present invention is the plasmid pJDB207.

Suitable marker genes for yeasts are, in particular, those which impart antibiotic resistance to the host or, in the case of auxotrophic yeast mutants, genes which complement host lesions. Corresponding genes impart, for example, resistance towards the antibiotic cycloheximide or provide for protrophy in an auxotrophic yeast mutant, for example the URA3, LEU2, HIS3 or, in particular, TRP1 gene. Yeast hybrid vectors furthermore preferably contain a replication start and a marker gene for a bacterial host, in particular E. coli, so that the construction and cloning of the hybrid vectors and their intermediates can take place in a bacterial host.

Expression control sequences which are suitable for expression in yeast are, for example, those of highly expressed yeast genes. Thus, the promoters of the TRP1 gene, the ADHI or ADHII gene, acid phosphatase (PH03 or PH05) gene, isocytochrome gene or a promoter involved with the glycolytic pathway, such as the promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used. Preferred vectors of the present invention contain promoters with transcriptional control, e.g. the promoters of the PH05, ADH II and CAPDH genes, which can be turned on or off by variation of the growth conditions. For example, the PH05 promoter can be repressed or derepressed solely by increasing or decreasing the concentration of inorganic phosphate in the medium.

Vectors suitable for replication and expression in mammalian cells are preferably provided with DNA from viral origin, e.g. from simian virus 40 (SV40), Rous sarcoma virus (RSV), adenovirus 2, bovine papilloma virus (BPV), papovavirus BK mutant (BKV), or mouse or human cytomegalovirus (CMV). Preferably, such vectors contain an origin of replication and an antibiotics resistance gene for propagation in E. coli together with an eukaryotic transcription regulatory sequence. In particular, such so-called shuttle vectors may be constructed from a pBR322 E. coli plasmid and SV40 and/or CMV enhancer and promoter regions. For example, the plasmid may contain the enhancer promoter unit of the mouse or human cytomegalovirus major immediate-early gene, the SV40 enhancer combined with the human α-globin promoter, and/or in addition inducible promoters, such as the ones derived from the heat shock or metallothionein genes. Further it is also possible to utilize promoter or control sequences which are normally associated with the desired gene sequence. An origin of replication may be provided either by construction of the vector to include an exogeneous origin, such as derived from SV40, other viral source or provided by the host cell chromosomal replication mechanism. If the vector is integrated into the host cell chromosome, the latter method is often more efficient.

In a preferred embodiment, the present invention relates to hybrid vectors capable of replication and phenotypical selection in a host strain comprising a promoter and a DNA encoding the desired protein, said DNA being positioned together with transcription start and termination signals as well as translation start and stop signals in said hybrid vector under the control of said promoter such that in a transformed host it is expressed to produce the polypeptide.

The invention also relates to a process for the preparation of a transformed host, which comprises transforming or transfecting a host with an expression vector containing a DNA of the invention regulated by an expression control sequence, and to the transformed or transfected hosts themselves.

Examples of suitable hosts are the above-mentioned microorganisms, such as strains of Saccharomyces cerevisiae, Bacillus subtilis and Escherichia coli. The transformation with the expression plasmids according to the invention is carried out, for example, as described in the literature, thus for *S. cerevisiae* [A. Hinnen, J. B. Hicks and G. R. Fink, Proc. Natl. Acad. Sci. USA, 75, 1929 (1978)], *B. subtilis* [Anagnostopoulos et al., J. Bacteriol. 81, 741 (1961)] and *E. coli* [M. Mandel et al., J. Mol. Biol. 53, 159 (1970)].

Accordingly, the transformation procedure of *E. coli* cells includes $Ca^{2+}$ pretreatment of the cells so as to allow DNA uptake, and incubation with the hybrid vector. The cells are transferred to a selective growth medium which allows separation of the transformed cells from the parent cells. Cells which do not contain the vector will not survive in such a medium. The transformation of yeast comprises, for example, the steps of (1) enzymatic removal of the yeast cell wall by means of glucosidases, (2) treatment of the obtained spheroplasts with the vector in the presence of polyethylene glycol and $Ca^{2+}$ ions and (3) regeneration of the cell wall by embedding the spheroplasts into agar. Preferably, the regeneration agar is prepared in a way to allow regeneration and selection of the transformed cells at the same time.

Further examples of suitable hosts are the above-mentioned mammalian cells, e.g. COS-7 cells, Hela cells or chinese hamster ovary (CHO) cells. The vectors are introduced into mammalian cells by transfection in the prescence of helper compounds, e.g. diethylaminoethyldextran, dimethyl sulfoxide, glycerol, polyethylene glycol or the like, or as co-precipitates of vector DNA and calcium phosphate. Further suitable methods include direct microinjection of vector DNA into the cell nucleus and electroporation, i.e. introduction of DNA by a short electric pulse increasing the permeability of cell membranes. The subsequent selection of transfected cells can be done using a selection marker which is either covalently integrated into the expression vector or added as a separate entity. Selection markers include genes which confer resistance to antibiotics, e.g. G-418 (neomycin) or hygromycin, or genes which complement a genetic Lesion of the host cell such as the absence of thymidine kinase or hypoxanthine phosphoribosyl transferase.

The transformed host cells are cultured by methods known in the art in a liquid medium containing assimilable sources of carbon, nitrogen and inorganic salts.

Various sources of carbon can be used for culture of the transformed hosts according to the invention. Examples of preferred sources of carbon are assimilable carbohydrates, such as glucose, maltose, mannitol or lactose, or an acetate, which can be used either by itself or in suitable mixtures. Examples of suitable sources of nitrogen are amino acids, such as casaminoacids, peptides and proteins and their degradation products, such as tryptone, peptone or meat extracts, yeast extracts, malt extract and also ammonium salts, for example ammonium chloride, sulfate or nitrate, which can be used either by themselves or in suitable mixtures. Inorganic salts which can also be used are, for example, sulfates, chlorides, phosphates and carbonates of sodium, potassium, magnesium and calcium.

The medium furthermore contains, for example, growth-promoting substances, such as trace elements, for example iron, zinc, manganese and the like, and preferably substances which exert a selection pressure and prevent the growth of cells which have lost the expression plasmid. Thus, for example, ampicillin is added to the medium if the expression plasmid contains an $amp^R$ gene. Such an addition of antibiotic substances also has the effect that contaminating antibiotic-sensitive microorganisms are destroyed. If a yeast strain which is auxotrophic in, for example, an essential amino acid is used as the host microorganism, the plasmid preferably contains a gene coding for an enzyme which complements the host defect. Cultivation of the yeast strain is performed in a minimal medium deficient in said amino acid.

Vertebrate cells are grown under tissue culture conditions using commercially available media optionally supplemented with growth-promoting substances and/or mammal sera. The cells are grown either attached to a solid support, e.g. a microcarrier or porous glass fibers, or free-floating in appropriate culture vessels.

Culturing is effected by processes which are known in the art. The culture conditions, such as temperature, pH value of the medium and fermentation time, are chosen so that a maximum titre of the polypeptide of the invention is obtained. Thus, an *E. coli* or yeast strain is preferably cultured under aerobic conditions by submerged culture with shaking or stirring at a temperature of about 20 to 40° C., preferably about 30° C., and a pH value of 4 to 8, preferably at about pH 7, for about 4 to 30 hours, preferably until maximum yields of the polypeptide of the invention are reached.

When the cell density has reached a sufficient value, the culture is interrupted and the polypeptide is isolated. If the polypeptide is fused with a suitable signal peptide sequence, it is excreted by the cell directly into the supernatant. Otherwise, the cells have to be destroyed, for example by treatment with a detergent, such as SDS, NP-40, Triton® or deoxycholic acid, or lysed with lysozyme, a similarly acting enzyme or with ultra-sound. If yeast is used as a host microorganism, the cell wall may be removed by enzymatic digestion with a glucosidase. Alternatively or additionally, mechanical forces, such as shearing forces (for example X-press, French press, Dyno mill) or shaking with glass beads or aluminium oxide, or alternating freezing, for example in liquid nitrogen, and thawing, for example to 30° to 40° C., as well as ultra-sound can be used to break the cells.

The cell supernatant or the solution obtained after centrifugation of the mixture obtained on breaking the cells, which contains proteins, nucleic acids and other cell constituents, is enriched in proteins, including the polypeptides of the invention, in a manner which is known per se. Thus, for example, most of the non-protein constituents are removed by polyethyleneimine treatment and the proteins including the polypeptides of the invention are precipitated, for example, by saturation of the solution with ammonium sulfate or with other salts. Otherwise, the cell supernatant or lysate is directly pre-purified using chromatographic methods.

The polypeptides of the invention are purified by a combination of chromatographic separations, preferably by a combination of ion exchange chromatography, gel filtration and reversed phase high performance liquid chromatography. Other separation methods may be included in the purification protocol, e.g. filtration or ultrafiltration with molecular weight cut-off membranes, affinity chromatography, chromatography on hydroxylapatite, chromatofocusing, and methods of dialyzing, dissolving and reprecipitating in suitable salt and/or buffer solutions and solvent mixtures.

A suitable carrier material for ion exchange chromatography may be of organic or inorganic origin, e.g. crosslinked agarose, dextran, polyacrylamide, styrene/divinylbenzene copolymer, cellulose, or the like. Preferably this carrier material bears basic functional groups, e.g. tertiary amino functions, quaternary ammonium groups, or slightly acidic groups, e.g. carboxymethyl functions. The carriers may be suitable for normal liquid chromatography, fast protein liquid chromatography (FPLC) or high performance liquid chromatography (HPLC). The separations and purifications with ion exchange chromatography are performed following established procedures, e.g. in aqueous buffer solutions of pH 4 to pH 9 containing increasing amounts of salt, for example sodium chloride.

Carrier material suitable for gel filtration or size exclusion chromatography includes cross-linked dextran, agarose, suitably modified polyacrylamide or silica, and the like. Optionally these carriers are modified with substituents bearing hydroxy functions, e.g. with 1-hydroxy- or 1,2-dihydroxy-lower alkyl groups. The chromatographic material is chosen so as to display optimal separation of peptides in the range of 50,000 to 100,000 Dalton molecular weight. Such gel filtration or size exclusion chromatography may be performed in columns suitable for normal liquid chromatography, FPLC or HPLC as above using aqueous buffer solutions around neutrality containing variable amounts of salt, e.g. sodium chloride.

Reversed phase chromatography is performed on silica-based carrier material bearing hydrophobic groups, e.g. alkyl groups of 1 to 20 carbon atoms, preferably 4, 8, 12 or 18 carbon atoms or mixtures of alkyl groups of 1 and 8 or 2 and 18 carbon atoms, respectively, or phenyl groups. Related to this method is the hydrophobic interaction chromatography, wherein agarose or a related material coated with alkyl groups of up to 12 carbon atoms and/or phenyl groups is used. These chromatographic techniques are applied using FPLC or HPLC. Solvents for processing of the polypeptides of the invention on silica-based reversed phase material are aqueous acids, e.g. aqueous trifluoroacetic acid, containing increasing amounts of a polar, water-miscible organic solvent, e.g. acetonitrile, lower alcohols, e.g. methanol, ethanol or propanol, tetrahydrofuran, and the like, preferably acetonitrile.

Affinity chromatography is also contemplated for the purification of the peptides of the invention, using a suitable carrier material, e.g. cross-linked agarose, dextran or polyacrylamide bearing molecules with high affinity for the desired proteins, for example antibodies, in particular monoclonal antibodies as described hereinbelow. The antibodies are then coupled to the carrier material in activated form by known methods. The purification of the desired proteins by affinity chromatography is performed in a manner known per se, e.g. in buffer solutions in a pH range of from approximately pH 5 to approximately pH 9 and/or salt solutions, for example NaCl solution, optionally containing surfactants, e.g. polyethylenesorbitan fatly acid esters, then eluting the desired proteins with buffer solutions in a pH range of from approximately pH 2 to approximately pH 5, such as glycine buffer, or pH gradients of differing composition or salt solutions, for example concentrated $NH_4$ SCN solution.

The antiviral properties of the proteins of the invention are useful for the therapy of and/or protection against viral infections. In particular, the proteins may be used for treating influenza and other respiratory tract virus infections, herpes virus infections, and rabies and hepatitis infection, optionally in combination with other antiviral agents. The proteins are applied in the form of pharmaceutical preparations that contain a therapeutically effective amount of the active ingredient optionally together or in admixture with inorganic or organic, solid or liquid, pharmaceutically acceptable carriers.

The pharmaceutical preparations according to the invention are those for enteral, e.g. rectal or oral, administration and preferably for parenteral, e.g. intranasal, intramuscular, subcutaneous or intravenous, administration to warm-blooded animals, for example humans.

Depending on the intended method of administration, the pharmaceutical preparations may be in unit dose form, for example in ampoules, vials, suppositories, dragees, tablets, capsules or nasal sprays in liquid or solid form.

The amount of the therapeutically effective compounds to be administered depends on the condition of the warm-blooded animal, for example the human, such as the body weight, the nature and severity of the disease and the general condition and also on the mode of administration, and is carried out in accordance with the assessment of the physician giving the treatment. The effective dose is in the order of magnitude of from 0.001 to 1 $\mu$g per kg of body weight per day.

The pharmaceutical preparations according to the invention contain the customary inorganic or organic, solid or liquid pharmaceutically acceptable carriers, optionally together with other therapeutically effective compounds and/or adjuncts. There are preferably used solutions or suspensions of the active ingredient, especially isotonic aqueous solutions or suspensions, or also lyophilized preparations which are dissolved in water shortly before use. The pharmaceutical preparations may be sterilized and/or contain preservatives, stabilizers, wetting agents, emulsifiers, solubilizers, viscosity-increasing substances, salts for regulating the osmotic pressure and/or buffers, and also other proteins, for example human serum albumin or human blood plasma preparations.

Further, the invention relates to monoclonal antibodies specific to the human proteins induced by interferon α or β as described hereinbefore, particularly to monoclonal antibodies which do not crossreact with the related mouse protein Mx induced by interferon, and to derivatives of such antibodies.

The monoclonal antibodies of the invention are preferably of murine origin, and are particularly mouse antibodies produced by mouse/mouse hybridoma cells.

Examples of monoclonal antibodies of the invention are the mouse monoclonal antibodies with the designation 885 S35.8.1, 885 S35.16.11, 885 S56.55.7.12.48, 885 S56.55.7.21.25, 885 S56.55.7.27.5, 885 S56.55.7.27.11, 885 S56.55.13, 885 S56.55.17, and 885 S56.67.15.

Preferred are the monoclonal antibodies with the designation 885 S35.8.1, 885 S56.55.13 and 885 S56.67.15, and derivatives thereof. These monoclonal antibodies are secreted by the corresponding hybridoma cell lines with the designation 885 S35.8.1, 885 S56.55.13 and 885 S56.67.15.

Derivatives of monoclonal antibodies of this invention are e.g. antibody fragments, radioactively labelled monoclonal antibodies, and conjugates of the monoclonal antibodies with enzymes, with fluorescent markers, or the like.

Fragments of monoclonal antibodies of this invention are e.g. Fab, Fab' or F(ab')$_2$ fragments, which retain their specificity for the antigenic determinants, i.e. which retain the specificity for the human interferon-induced proteins as described hereinbefore.

Radioactively labelled monoclonal antibodies contain e.g. radioactive iodine ($^{123}$I, $^{125}$I, $^{131}$I), carbon ($^{14}$C), sulfur ($^{35}$S), tritium ($^3$H) or the like. Preferred are monoclonal antibodies labelled with radioactive iodine.

Antibody conjugates of the invention are e.g. conjugates of monoclonal antibodies or fragments thereof with enzymes such as horseradish peroxidase, alkaline phosphatase, B α-D-galactosidase, glucoseoxidase, glucoamylase, carboanhydrase, acetylcholinesterase, lysozyme, malate dehydrogenase or glucose-6-phosphate dehydrogenase, with fluorescent markers, e.g. fluorescein, or with avidin or biotin. In such conjugates the antibody is bound to the enzymes or fluorescent marker directly or by the way of a spacer or linker group. Preferred are conjugates of monoclonal antibodies with the enzymes horseradish peroxidase or alkaline phosphatase.

The monoclonal antibodies of the invention and derivatives thereof are obtained by processes known per se, characterized in that hybridoma cells secreting said monoclonal antibodies a) are cultivated in vitro and the monoclonal antibodies isolated from the culture supernatant, or b) are propagated in vivo in a suitable mammal and the monoclonal antibodies recovered from body fluids of said mammal, and, if desired, c) the obtained monoclonal antibodies are converted into a derivative thereof.

Suitable culture media for the in vitro cultivation according to process a) are standard culture media such as Dulbecco's Modified Eagle Medium or RPMI 1640 Medium, optionally replenished by a mammal serum, e.g. fetal calf serum, or other growth-sustaining supplements, e.g. 2-aminoethanol, insulin, transferrin, low density lipoprotein, oleic acid and the like, and trace elements. The isolation of the monoclonal antibodies is accomplished by precipitating the protein contained in the culture supernatants by ammonium sulfate or the like, followed by purifying the immunoglobulins by standard chromatographic methods, such as gel filtration, ion exchange chromatography, chromatography on DEAE cellulose, or immunoaffinity chromatography.

In vitro production allows scale-up to give large amounts of the desired antibodies. Techniques for large scale hybridoma cultivation are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges.

Large amount s of the desired mono clonal antibodies can also be obtained by the propagation of hybridoma cells according to process b). Cell clones are injected into syngeneic mammals, which causes antibody-producing tumors to grow. After one to three weeks the desired monoclonal antibodies are recovered from body fluids of said mammal. As an example hybridoma cells derived from Balb/c mice are intraperitoneally injected into Balb/c mice optionally pretreated with a hydrocarbon such as pristane, and after one to two weeks, ascites fluid of these mice is collected. The desired monoclonal antibodies are isolated from the body fluids by methods known per se, e.g. by precipitating the proteins with ammonium sulfate or the like, followed by purifying the immunoglobulins by standard chromatographic methods, such as gel filtration, ion exchange chromatography, chromatography on DEAE cellulose, or immunoaffinity chromatography.

Fragments of monoclonal antibodies, for example Fab, Fab' or F(ab')$_2$ fragments, which retain their specificity towards the human interferon-induced proteins as described hereinbefore, can be obtained from the monoclonal antibodies pre pared according to process a) or b) by methods known per se, e.g. by digestion with enzymes such as pepsin or papain and/or cleavage of disulfide bonds by chemical reduction.

Monoclonal antibodies labelled with radioactive iodine are prepared by iodination methods known in the art, e.g. by labelling monoclonal antibodies with radioactive sodium or potassium iodide and a chemical oxidant, such as sodium hypochlorite, chloramine T or the like, or an enzymatic oxidant, such as lactoperoxidase or glucose oxidase and glucose. Radioactively labelled monoclonal antibodies o f the invention are also prepared by adding radioactively labelled nutrients to the culture media of the in vitro cultivation of step a). Such labelled nutrients contain e.g. radioactive carbon ($^{14}$C), tritium ($^3$H), sulfur ($^{35}$S) or the like, and are for example L-($^{14}$C)-leucine, L-($^3$H)-leucine or L-($^{35}$S)-methionine.

Conjugates of monoclonal antibodies of the invention are prepared by methods known in the art, e.g. by reacting a monoclonal antibody prepared according to process a) or b) or a fragment thereof prepared as described hereinbefore with the enzyme in the presence of a coupling agent, e.g. glutaraldehyde, periodate, N,N'-o-phenylenedimaleimide, N-(m-maleimidobenzoyloxy)-succinimide, N-(3-[2'-pyridyldithio]-propionoxy)-succinimide, N-ethyl-N'-(3-dimethylaminopropyl)-carbodiimide or the like. Conjugates with avidin are prepared likewise. Conjugates with biotin are prepared e.g. by reacting monoclonal antibodies with an activated ester of biotin such as the biotin N-hydroxysuccinimide ester. Conjugates with fluorescent markers are prepared in the presence of a coupling agent, e.g. those listed above, or by reaction with an isothiocyanate, preferably fluorescein-isothiocyanate.

The invention further relates to hybridoma cell lines, characterized in that they secrete monoclonal antibodies with specificity for the human interferon-induced proteins as described hereinbefore.

In particular, the invention relates to cell lines, which are hybrids of myeloma cells and B lymphocytes of a mammal immunized with purified human interferon-induced protein with apparent molecular weight of 78 kDa. Preferentially, these cell lines are hybrids of mouse myeloma cells and B lymphocytes of a syngeneic mouse immunized with the protein.

Examples of such cell lines are the hybridoma cell lines with the designation 885 S35.8.1, 885 S35.16.11, 885 S56.55.7.12.48, 885 S56.55.7.21.25, 885 S56.55.7.27.5, 885 S56.55.7.27.11, 885 S56.55.13, 885 S56.55.17, and 885 S56.67.15.

These hybridoma cell lines are hybrids of the mouse myeloma cell line Sp2/0-Ag14 and of B lymphocytes of the spleen of Balb/c mice immunized with the purified human interferon-induced protein from Namalwa cells as described hereinbefore. They are stable cell lines and secrete the monoclonal antibodies with the corresponding designation. The cell lines may be kept in culture or deep-frozen in liquid nitrogen and reactivated by thawing.

Particularly preferred are the hybridoma cell lines with the designation 885 S35.8.1, 885 S56.55.13 and 885 S56.67.15, which have been deposited on Apr. 9, 1986 at the "Collection Nationale de Cultures de Microorganismes", Institut Pasteur, Paris, under the number I-545, I-543, and I-544, respectively.

The invention relates also to a process for the production of hybridoma cell lines secreting monoclonal antibodies with specificity for the interferon-induced proteins as described hereinbefore, characterized in that a suitable mammal is immunized with a purified protein, optionally with an antigenic carrier, antibody-producing cells of this mammal are fused with myeloma cells, the hybrid cells obtained in the fusion are cloned, and cell clones secreting the desired antibodies are selected.

Preferred mammals for the immunization are mice, particularly HR-mice. The immunizations are performed e.g. by implanting an antigenic carrier, e.g. a nitrocellulose piece, containing purified 78 kDa protein from induced Namalwa cells, and further injecting between 2 μg and 10 μg of the protein two to ten times parenterally, such as intraperitoneally and/or subcutaneously, at intervals of 7 to 30 days. The injections optionally contain an adjuvant stimulating the lymphocyte production such as complete or incomplete Freund's adjuvant and/or an adjuvant peptide.

Antibody-producing cells of the immunized mammals, preferably spleen cells, taken two to five days after the final booster injection, are fused with myeloma cells of a suitable cell line in the presence of a fusion promoter. Several suitable myeloma cell lines are known in the art. Preferred are myeloma cell lines lacking the enzyme hypoxanthine guanine phosphoribosyl transferase (HGPRT) or the enzyme thymidine kinase (TK), which therefore do not survive in a selective culture medium containing hypoxanthine, aminopterin and thymidine (HAT medium). Particularly preferred are myeloma cells and derived cell lines that do not survive in HAT medium and do not secrete immunoglobulins or fragments thereof, such as the cell lines X63-Ag8.653 or Sp2/0-Ag14. Fusion promoters considered are e.g. Sendai virus or other paramyxo viruses, optionally in UV-inactivated form, calcium ions, surface-active lipids such as lysolecithin, or polyethylene glycol. Preferentially, the myeloma cells are fused with a three- to twentyfold excess of spleen cells from immunized mammals in a solution containing about 30% to about 60% polyethylene glycol of a molecular weight between 1000 and 4000.

After the fusion, the cells are resuspended and cultivated in selective HAT medium. Thereby, only hybridoma cells will survive, because they combine the ability to grow and replicate in vitro, which ability is inherited from myeloma cells, with the missing HGPRT or TK genes essential for the survival in the HAT medium, which genes are inherited from the antibody-producing spleen cells of the immunized mammals.

Suitable culture media for the expansion of hybridoma cells are the standard culture media, such as Dulbecco's Modified Eagle Medium, minimum essential medium, RPMI 1640 medium and the like, optionally replenished by serum, e.g. 10 to 15% fetal calf serum. Preferentially feeder cells are added at the beginning of the cell growth, e.g. normal mouse peritoneal exsudate cells, spleen cells, marrow bone macrophages, or the like. The culture media are supplemented with selective HAT medium at regular interval in order to prevent normal myeloma cells overgrowing the hybridoma cells.

The hybridoma cell culture supernatants are screened for the desired monoclonal antibodies, preferentially with an enzyme immunoassay, e.g. a dot-ELISA assay, or a radioimmunoassay. Positive hybridoma cells are cloned, e.g. by limiting dilution, preferentially twice or more. Optionally, hybridoma cells are passaged through animals, e.g. mice, by i.p. injection and harvesting of ascites, which stabilizes hybridomas and improves growth characteristics. The cloned cell lines may be frozen in a conventional manner.

The monoclonal antibodies of the invention and/or their derivatives are useful for the qualitative and quantitative determination of the interferon-induced human proteins as described hereinbefore.

For instance, the monoclonal antibodies or derivatives thereof, such as enzyme conjugates or radioactive derivatives, can be used in any of the known immunoassays, which rely on the binding interaction between the antigenic determinant of the proteins of the invention and the monoclonal antibodies. Examples of such assays are radioimmunoassays (RIA), enzyme immunoassays, e.g. enzyme-linked immunoadsorbent assay (ELISA), immunofluorescence, immunoprecipitation, latex agglutination, and hemagglutination. Such immunoassays are useful e.g. in the monitoring of the production and purification of the desired proteins from natural sources or genetically engineered microorganisms and in the qualitative and quantitative determination of the proteins in biological fluids, e.g. of patients under therapy with a protein of the invention or with interferon, or in need of such therapy.

The monoclonal antibodies according to the invention can be used as such or in the form of radioactively labelled derivatives in a radioimmunoassay (RIA). Any of the known modifications of an RIA can be used, for example RIA in homogeneous phase, solid phase RIA or heterogeneous RIA, single RIA or double (sandwich) RIA with direct or indirect (competitive) determination of the protein of the invention. There is preferred a sandwich RIA in which a suitable carrier, for example the plastics surface of a microtitre plate or of a test tube, for example of polystyrene, polypropylene or polyvinyl chloride, glass or plastics beads, filter paper, or dextran, cellulose acetate or nitrocellulose sheets or the like, is coated with a monoclonal antibody of the invention by simple adsorption or optionally after activation of the carrier, for example with glutaraldehyde or cyanogen bromide, and incubated with the test solution and a solution of a monoclonal antibody radioactively labelled with $^{125}I$, the dissolved monoclonal antibody recognising another epitope of the proteins of the invention than the carrier-bound monoclonal antibody, and the amount of the proteins of the invention is determined by measuring the radioactivity bound to the carrier.

Particularly preferred is a sandwich radioimmunoassay as described hereinbefore, wherein a monoclonal antibody of the invention is bound to a bead, for example a polystyrene bead, this coated bead is incubated in a test or standard solution containing interferon induced human proteins and is finally developed with a radiolabelled monoclonal antibody recognizing a different epitope.

The monoclonal antibodies according to the invention can be used as such or in the form of enzyme-conjugated derivatives in an enzyme-immunoassay. Such immunoassays include test procedures in which enzyme-labelled monoclonal antibody derivatives according to the invention or enzyme-labelled antibodies known per se that recognize and bind an epitope of the antibodies according to the invention are used.

There is preferred an ELISA (enzyme-linked immunoadsorbent assay) in which a carrier as described above for an RIA is coated with a monoclonal antibody according to the invention, incubated with a test solution containing an interferon-induced human protein and then with a polyclonal serum to the protein, for example sheep serum, and, finally, the bound antibodies of the polyclonal serum are developed by enzyme-labelled antibodies that recognize and bind to them, and the amount of the protein bound is determined by an enzyme substrate reaction. Such an enzyme-labelled antibody is, for example, a phosphatase-labelled goat-anti-sheep immunoglobulin.

There is also preferred an ELISA in which a carrier coated with a monoclonal antibody according to the invention is incubated with a test solution and with a solution of a monoclonal antibody that is conjugated with an enzyme, the dissolved monoclonal antibody recognizing a different epitope of the interferon-induced human protein than does the carrier-bound monoclonal antibody. By an enzyme substrate reaction that results, for example, in a color change and can be observed by eye or with optical measuring devices, the amount of bound enzyme, which is proportional to the amount of the protein in the test solution, is measured.

Particularly preferred is an enzyme immunoassay called immunodot analysis, in which test or standard solutions containing the interferon-induced human protein are spotted on a microporous carrier with high intrinsic affinity for polypeptides, e.g. on nitrocellulose, the carrier bearing one or several dots of said samples is incubated in a solution of a monoclonal antibody of the invention, then in a solution of an enzyme-labelled second antibody that recognizes and binds the monoclonal antibody of the invention and finally in a solution of an enzyme substrate which leads to a detectable signal, e.g. a colored substance. Such an enzyme-labelled second antibody is e.g. rabbit anti-mouse immunoglobulin conjugated with horseradish peroxidase which can be developed with suitable enzyme substrates such as 4-chloro-1-naphthol or the like.

The monoclonal antibodies according to the invention can be used as such or in the form of derivatives conjugated with fluorescent markers in immunofluorescence tests. Such immunofluorescence tests include procedures wherein monoclonal antibody derivatives according to the invention, e.g. derivatives conjugated with fluorescein, or fluorescent marker-labelled antibodies known per se that recognize and bind an epitope of the monoclonal antibodies according to the invention are used.

There is preferred an immunofluorescence test in which a carrier as described above for an RIA is coated according to standard methods with cells to be tested for the presence of a protein of the invention, the cells are fixed and permeabilized to allow interaction of proteinaceous material inside the cell with solutions applied, then incubated with a solution of a monoclonal antibody derivative according to the invention conjugated with a fluorescent marker, or incubated with a solution of a monoclonal antibody of the invention followed by a solution of a fluorescent marker-labelled second antibody that recognizes and binds the monoclonal antibody of the invention, e.g. a fluorescein-labelled rabbit anti-mouse immunoglobulin. The presence of a protein of the invention is then detected and the protein localized by standard fluorescence microscopy or flow cytometry.

The monoclonal antibodies according to the invention can be used as such or in the form of radiolabelled derivatives in immunoprecipitation tests. Preferred is an immunoprecipitation test wherein cells to be tested for their ability to produce a protein of the invention are grown in culture media containing radioactively labelled nutrients, e.g. nutrients labelled with radioactive carbon ($^{14}$C), tritium ($^3$H), sulfur ($^{35}$S) or the like, for example ($^{35}$S)-methionine, then lysed to obtain a solution of radiolabelled proteinaceous material produced by the cells. This solution is incubated with a solution of a monoclonal antibody of the invention, any complex between radiolabelled protein formed in the cell and the monoclonal antibody of the invention precipitated or, preferably, adsorbed on affinity chromatography material with high affinity for the monoclonal antibodies of the invention, e.g. chromatography material coupled to protein A or to an antibody recognizing and binding the monoclonal antibodies of the invention, e.g. to rabbit anti-mouse immunoglobulin, and the protein/antibody complex isolated from the precipitate or the affinity chromatography material. The presence of the radiolabelled protein is then confirmed by usual analytical methods, e.g. SDS polyacrylamide gel electrophoresis with fluorography, under conditions dissociating the protein/antibody complex.

The use according to the invention of monoclonal antibodies and derivatives thereof as described hereinbefore for the qualitative and quantitative determination of the human interferon-induced proteins also includes other immunoassays known per se, for example latex agglutination with antibody-coated or antigen-coated latex particles or hemagglutination with antibody-coated or antigen-coated red blood corpuscles or the like.

The invention relates also to test kits for the qualitative and quantitative determination of human interferon-induced proteins with apparent molecular weight of 78 kDa containing monoclonal antibodies of the invention and/or derivatives thereof and, optionally, other monoclonal or polyclonal antibodies and/or adjuncts.

Test kits according to the invention for a radioimmunoassay contain, for example, a suitable carrier, uncoated or coated with a monoclonal antibody of the invention, optionally freeze-dried or concentrated solutions of a monoclonal or polyclonal antibody to a protein of the invention and/or a radiolabelled derivative thereof, standard solutions of this protein, buffer solutions and, optionally, polypeptides and detergents for preventing non-specific adsorption and aggregate formation, pipettes, reaction vessels, calibration curves, instruction manuals and the like.

Test kits according to the invention for an enzyme immunoassay contain, for example, a suitable carrier, e.g. microtiter plates or nitrocellulose sheets, optionally freeze-dried or concentrated solutions of a monoclonal antibody to a protein of the invention and of an enzyme-labelled monoclonal or polyclonal antibody to this protein or to a first antibody recognizing the protein, enzyme substrates in solid or dissolved form, standard solutions of a protein of the invention, buffer solutions and, optionally, polypeptides and detergents, pipettes, reaction vessels, calibration curves, color scale tables, instruction manuals and the like.

Test kits according to the invention for an immunofluorescence test contain, for example, a suitable carrier, e.g. plastic coverslips or glass slides, optionally freeze-dried or concentrated solutions of a monoclonal antibody to a protein of the invention and of a fluorescein-labelled polyclonal antibody recognizing the monoclonal antibody, buffer solutions and, optionally, standard solutions containing a protein of the invention, polypeptides and detergents, pipettes, reaction vessels, instruction manuals and the like.

Test kits according to the invention for an immunoprecipitation test contain, for example, a suitable carrier, e.g. plastic or glass plates, optionally freeze-dried or concentrated solutions of a monoclonal antibody to a protein of the invention, solutions of radiolabelled nutrients, e.g. $^{35}$S-methionine, tissue culture solutions, buffer solutions, optionally freeze-dried or concentrated solutions of an interferon α or β, and, optionally, standard solutions containing a protein of the invention, affinity chromatography material binding the monoclonal antibody in an antigen/antibody complex, detergents and polypeptides, pipettes, reaction vessels, instruction manuals and the like.

The monoclonal antibodies and antibody derivatives of the invention are used for the qualitative and quantitative determination of the human 78 kDa protein induced by interferon α or β, preferably in enzyme immunoassays, immunofluorescence tests or immunoprecipitation tests. The reliable determination of the amount of human 78 kDa in biological fluids, tissue sections and cells allows a simple surveillance of a therapy with the human 78 kDa protein or of a therapy with interferon α or β. Furthermore, the monoclonal antibodies and antibody derivatives can be used in the isolation and purification of human 78 kDa protein from natural sources or from recombinant host cells by immunoaffinity chromatography.

The following examples illustrate the invention, but do not limit it to any extent.

The abbreviations used in the examples have the following meaning:

| | |
|---|---|
| ATP | adenosine triphosphate |
| BSA | bovine serum albumin |
| cDNA | complementary DNA |
| cpm | counts per min (radioactive decay) |
| dA | 2'-deoxyadenosine |
| dATP | 2'-deoxyadenosine triphosphate |
| dC | 2'-deoxycytidine |
| dCTP | 2'-deoxycytidine triphosphate |
| dG | 2'-deoxyguanosine |
| dGTP | 2'-deoxyguanosine triphosphate |
| DNA | deoxyribonucleic acid |
| dNTP | mixture of dATP, dCTP, dGTP and dTTP |
| ds DNA | double-stranded DNA |
| dT | (2'-deoxy-)thymidine |
| dTTP | thymidine triphosphate |
| EDTA | ethylenediamine-tetraacetic acid |
| FCS | foetal calf serum |
| HAT | hypoxanthine/aminopterin/thymidine |
| IFN | interferon |
| kDa | kilo-Dalton (molecular weight) |
| mRNA | messenger RNA |
| PBS | phosphate buffered saline |
| RNA | ribonucleic acid |
| rpm | revolutions per min |
| SDS | sodium dodecyl sulfate |
| TBS | Tris buffered saline |
| Tris | tris(hydroxymethyl)aminomethane |
| tRNA | transfer RNA |

The following buffer solutions and media are used:

| | |
|---|---|
| Denhardt solution | 0.1% polyvinylpyrrolidone (PVP-360, Sigma), 0.1% Ficoll 400 (Pharmacia), 0.1% BSA. |
| hypotonic buffer | 5 mM Tris.HCl, pH 7.4, 1.5 mM KCl, 2.5 mM $MgCl_2$. |
| LB medium | 1% Bacto ® tryptone (Difco), 0.5% Bacto ® yeast extract (Difco), 170 mM NaCl, adjusted to pH 7.5 with NaOH. |
| ligation buffer | 50 mM Tris HCl, pH 8, 7 mM $MgCl_2$, 1 mM dithiothreitol. |
| mung bean nuclease buffer | 30 mM NaOAc, pH 5, 50 mM NaCl, 1 mM $ZnCl_2$, 5% glycerol. |
| PBS | 136 mM NaCl, 2 mM KCl, 8 mM $Na_2HPO_4$, 1.4 mM $KH_2PO_4$. |
| SSC buffer | 15 mM sodium citrate, 150 mM NaCl, adjusted to pH 7.0 with NaOH. |
| TBS | 10 mM Tris.HCl, pH 7.6, 0.15 M NaCl. |
| TE buffer | 10 mM Tris.HCl, pH 7.5, 1 mM EDTA. |

EXAMPLE 1

Induction of Namalwa Cells with Interferon 1.1 Cell Line:

Namalwa cells ATCC CRL 1432 are cultured in a medium consisting of RPMI 1640 medium supplemented with 2 g/l $NaHCO_3$, penicillin ($10^5$ units/liter), streptomycin (100 mg/liter) and 10% inactivated FCS (inactivation: 30 min at 56° C.), in suspension culture in one liter Spinner flasks (Bellco). The cells are seeded at a concentration of $5 \times 10^5$ cells per ml, and subcultured when the concentration reaches $20 \times 10^5$ cells per ml (about three times a week).

1.2 Incubation with Interferon Alpha:

2 liter of medium are seeded with Namalwa cells at a concentration of $5 \times 10^5$ cells per ml. They are cultured in a 3 liter Spinner flask for 3 days at 37° C. At the end of the exponential growth, the concentration of cells reaches 2 to $3 \times 10^6$ cells per ml. The cells are centrifuged at 800×g for 30 min, then resuspended in 2 liter of culture medium and incubated for 6 h at 37° C. Interferon $5_1$ ($\alpha/\beta$ type prepared according to EP-A 76 489) is added at a final concentration of 5000 international units per ml, and the cultures further incubated at 37° C. for 20 h.

1.3 Harvest of Cells:

The cells are centrifuged for 30 min at 1000×g. The cell pellet is washed with PBS. The cells are centrifuged for 10 min at 800×g, and the pellet suspended in hypotonic buffer. The cells are centrifuged for 10 min at 800×g, and the pellet is frozen rapidly on dry ice and kept at −20° C.

EXAMPLE 2

Isolation and Purification of the 78 kDa Protein 2.1 Protein Extraction:

Thawed cells of Example 1 are lysed at 20° C. with 200 ml of buffer 50 mM Tris.HCl, pH 7.4, and 4 M NaCl. The lysate is clarified by ultracentrifugation at 80,000×g for 1 h. The IFN-induced protein is in the supernatant. Ammonium sulfate is slowly added to the supernatant to a final concentration of 30%. The proteins are precipitated for 1 h at 20° C. The precipitate containing the IFN-induced protein is centrifuged for 15 min at 3000×g, then suspended in 3 ml buffer containing 50 mM Tris.HCl, pH 8, 150 mM mercaptoethanol, 6 M urea and 2% NP-40. The suspension is extensively dialysed against the same buffer. Most of the IFN-induced protein remains insoluble.

2.2 Preparative Gel Electrophoresis:

The insoluble proteins are centrifuged and dissolved in sample buffer [U. K. Laemmli & M. Favre, J. Mol. Biol. 80, 575 (1973)]. The slab gels (1.5 mm thick and 110 mm long) are prepared as described by Laemmli & Favre. The separating gel contains 12% acrylamide and 0.32% bis-acrylamide. At the end of the electrophoresis the proteins are visualized by dipping the gel into ice-cold 0.25 mM KCl. The piece of gel containing proteins of molecular weight between 70 kDa and 85 kDa is cut out. The gel is extensively washed with $H_2O$, equilibrated with 50 mM N-ethylinorpholinium acetate, pH 8.5, and 0.1% SDS. Finally the gel is sliced in 2 nm urea, 50 mM N-ethylmorpholinium acetate, pH 8.5, 2% SDS, and 50 mM dithiothreitol. The mixture is incubated for 1 h at 37° C.

2.3 Electrodialysis of Proteins from the Gels:

An ISCO sample concentrator (Model 1750) is used to elute the proteins from the gel pieces, as described by A. J. Brown & J. C. Bennett [Methods in Enzymology 91, 450 (1983)]. N-Ethylmorpholinium acetate, pH 8.5, containing 0.01% SDS and 1 mM dithiothreitol is used as buffer in the outer (0.1 M) and inner (0.05 M) chambers of the concentrator tank, respectively. The eluted proteins are precipitated with 5 volumes of acetone.

2.4 Final Purification by Polyacrylamide Gel Electrophoresis in Two Dimensions:

The two-dimensional system combining non-equilibrium pH gradient electrophoresis (NEPHGE) with SDS-polyacrylamide gel electrophoresis is used as described by P. Z. O'Farrell et al. [Cell 12, 1133 (1977)]. The proteins of the acetone precipitate (Example 2.3) are solubilized in "lysis buffer A" [P. H. O'Farrell, J. Biol. Chem. 250, 4007 (1975)] and applied to the acidic end of the non-equilibrium pH gradient electrophoresis gel, which contains 2% ampholytes, pH 3–10. The electrophoresis is run for 5 h at 500 V. The separating gel for slab gel electrophoresis in the second dimension contains 12% acrylamide and 0.32% bis-acrylamide. Proteins are visualized by dipping the gel into ice-cold 0.25 M KCl. The piece of gel containing the IFN-induced protein, a single spot free of other proteins, is cut out and processed for electrodialysis as described above in Example 2.3. The purified protein is precipitated with 5 volumes of acetone.

EXAMPLE 3

Characterization of the Purified 78 kDa Protein:
3.1 SDS Polyacrylamide Gel Electrophoresis The purified protein is analyzed by one-dimensional gel electrophoresis on 12% polyacrylamide gels in the usual way. The bands are stained with Coomassie blue G-250. The molecular weight markers (from Bio-Rad) run in parallel are: lysozyme (14 kDa), soybean trypsin inhibitor (21.5 kDa), carbonic anhydrase (31 kDa), ovalbumin (45 kDa), bovine serum albumin (66.2 kDa) and phosphorylase B (92.5 kDa). The purified IFN-induced protein is homogenous in this type of analysis and migrates as a protein with approximate molecular weight 78 kDa.

The isoelectric point of the IFN-induced protein is 6.3 as determined in the system described by P. H. O'Farrell [J.Biol.Chem. 250, 4007 (1975)].
3.2 N-terminal Amino Acid Sequence 32 µg of the protein are subjected to an amino acid sequence analysis in a Beckman 8906 sequencer in the manner described by J. Y. Chang et al. [Biochem. J. 211, 173 (1983)].

The following N-terminal sequence is found: Val-Val-$X_3$-Glu-Val-Asp-Ile-Ala-Lys-Ala-Pro-Lys-Ala. (SEQ ID NO.12).

The third amino acid could not be identified.
3.3 Total Amino Acid Composition:

Total amino acid composition is determined following a procedure of J. Y. Chang, R. Knecht & D. G. Braun [Methods in Enzymology, Vol. 91, 41–48 (1983)]. Briefly, the protein is hydrolyzed with 6 M HCl, derivatized with 4'-dimethylamino-azobenzene-4-sulfonyl chloride in sodium bicarbonate buffer, and injected on a Zorbax-ODS® high performance liquid chromatography (HPLC) column. The amount of each amino acid is determined by comparison with a standard sample. The results are collected in Table 1.

EXAMPLE 4

Isolation of mRNA from Cells Induced with Interferon 4.1 Induction of Human Embryonic Foreskin Cells with Interferon Alpha:

Human embryonic foreskin diploid cells (Flow No. 7000) are cultured in Earl's minimum essential medium supplemented with $NaHCO_3$ (2 g/liter), penicillin ($10^5$ units/liter), streptomycin (100 mg/liter) and 10% inactivated FCS (inactivation: 30 min at 56° C.) in plastic dishes of 14 cm diameter. Confluent cell monolayers are subcultured in a trypsin/EDTA solution (Gibco) at a split ratio of 1 to 3. Confluent cell monolayers are incubated in fresh medium containing recombinant interferon $5_1$ (α/B type prepared according to EP-A 76 489) at a final concentration of 1000 international units per ml for 4.5 h at 37° C.
4.2 Purification of Cytoplasmic RNA:

The cell monolayer of Example 4.1 is washed with PBS at 4° C. and incubated in hypotonic buffer for 2 min at 4° C. The cytoplasmic extract is obtained by lysis of cells with the hypotonic buffer containing 1%. deoxycholate and 1% NP-40 for 5 min at 4° C. The extract is centrifuged at 25,000×g for 5 min. To the supernatant (45 ml) are added 16 mg proteinase K, 720 mg NaCl, 1.8 ml 1 M Tris.HCl, pH 7.4, and 6.8 ml 10% SDS. The mixture is kept at 20° C. for 4 h. The RNA is extracted 3 times with phenol saturated with a solution of 0.1 M Tris.HCl, pH 9, and 0.1% oxyquinoline. NaCl is added to the aqueous phase (final concentration 0.1 M) and the RNA is precipitated with 2 volumes of ethanol at −20° C.
4.3 Further Purification of Total RNA:

2 mg RNA of Example 4.2 in 50% formamide are layered onto a linear 5 to 20% sucrose gradient in 5 mM EDTA, 0.01 M Tris.HCl, pH 7.5, 0.2% SDS, 0.05 M NaCl, and 50% formamide. The gradients are centrifuged at 20° C. for 16 h at 40,000 rpm in a Beckman SW41 Ti rotor. 1 ml fractions are collected, made up to 0.1 M NaCl, and the RNA precipitated with 2 volumes of ethanol. An RNA aliquot of each fraction is translated in a reticulocyte lysate cell free system (Amersham International No. N90) according to the instructions of the manufacturer. Proteins synthesized in vitro and labelled with $^{35}$S-methionine are separated by polyacrylamide gel electrophoresis in two dimensions, and detected by fluorography. mRNA directing the synthesis of an IFN-induced protein of apparent molecular weight 78 kDa is reproducibly found in fractions 8 and 9, at sedimentation values between 18S and 28S. Poly(A) mRNA of fractions 8 and 9 is purified by chromatography on oligo(dT) cellulose.

EXAMPLE 5

Preparation and Screening of a cDNA Library

Starting with purified mRNA of Example 4.3, a cDNA library is prepared following the method of U. Gubler and B. J. Hoffman, Gene 25, 263–269 (1983) with some modifications.

For the synthesis of the first strand cDNA, the purified poly(A) mRNA of fractions 8 and 9 (Example 4.3, 150 µg/ml) is incubated in a volume of 20–40 µl containing 50 mM Tris.HCl, pH 8.3, 10 mM $MgCl_2$, 10 mM dithiothreitol, 1.25 mM of each dGTP, dATP and dTTP, 0.5 mM dCTP, 20 µCi of α-$^{32}$P-dCTP (ca. 3000 Ci/mmol) and 100 µg/ml of oligo($dT_{12-18}$) with 3000 units per ml of "Super" reverse transcriptase from avian myeloblastosis virus (Anglian Biotechnology-Stehelin) for 30 min at 43° C. The reaction is stopped by adding EDTA, the products extracted with phenol and precipitated with ethanol. For second strand synthesis, the single-stranded cDNA (500 ng) is incubated in 100 µl of 20 mM Tris.HCl, pH 7.5, 5 mM $MgCl_2$, 10 mM $(NH_4)_2SO_4$, 100 mM KCl, 0.15 mM β-nicotinamide adenine dinucleotide, 50 µg/ml BSA and 40 mM of each dNTP with 8.5 units/ml of E. coli RNase H, 230 units/ml DNA polymerase I and 10 units/ml $T_4$ DNA ligase overnight at 14° C. The ds cDNA is isolated as above.

The ds cDNA (100 ng in 40 µl) is tailed with dCTP (0.9 mM) in 200 mM potassium cacodylate, pH 6.9, 1 mM $CoCl_2$ and 5 mg/ml BSA with 30 units of terminal transferase for 60 min at 37° C., followed by heat inactivation. This dC-tailed cDNA is annealed to dG-tailed, PstI cut pBR322 (BRL) in 50 µl TE buffer/0.15 M NaCl at total DNA concentrations of 0.5 µg/ml DNA for 90 min at 58° C. $CaCl_2$ treated E. coli MC1061 are transformed with this vector. The cells are plated and handled at high density on nitrocellulose filters laid on agar plates as described by D. Hanahan and M. Meselson [Methods Enzymol. 100, 333–342 (1983)].

An oligodeoxynucleotide mixture is synthesized on the basis of the known partial amino acid sequence of Example 3.2, namely the sequence Glu-Val-Asp-Ile-Ala-Lys-Ala. (SEQ ID NO.13) The 20-mer oligodeoxynucleotide mixture of the composition 5'-GCYTTIGCQATRTCIACYTC-3', (SEQ ID NO.14) wherein A, T, G, C and I stand for adenosine, thymidine, guanosine, cytosine and inosine, respectively, Y and R for pyrimidines (T, C) and purines (A, C), respectively, and Q for A, G and T, is synthesized following the procedure of Y. Ike et al., Nucleic Acid Research 11, 477 (1983). The 5' ends of the oligodeoxynucleotides are rendered radioactive using $\gamma$-$^{32}$P-dATP (5000 Ci/mmol) and polynucleotide kinase (Pharmacia) to $2-5 \times 10^8$ cpm/µg using standard procedures [T. Maniatis, E. F. Fritsch and J. Sambrook, "Molecular cloning, a laboratory manual", Cold Spring Harbor Laboratory, 1982].

Duplicate replicas of the bacterial clones of the cDNA library are hybridized with the above nucleotide mixture following the method of Hanahan and Meselson [loc. cit.] in a medium containing 6×SSC, 5× Denhardt solution, 250 µg/ml tRNA, 50 units/ml heparin and 0.1% SDS at 47° C. After hybridization, the filters are washed four times in 6×SSC and 0.5% SDS for 20 min at 20° C. and 5 min at 47° C.

Clone B1,1 containing a DNA plasmid with an insert of approximately 850 base pairs is found to hybridize with the oligonucleotide probe and is grown in LB medium supplemented with 15 µg/ml tetracycline at 37° C.

EXAMPLE 6

Isolation of Plasmid DNA 800 ml of LB medium supplemented with 15 µg/ml tetracycline is inoculated with 1 ml of clone B1,1 (Example 5) and cultured at 37° C. to an optical density $OD_{550}$ of 0.7 (approx. 5 h). 200 µg/ml chloramphenicol dissolved in ethanol are added and culturing continued at 37° C. overnight. The mixture is centrifuged for 20 min at 0° C. with 4000 rpm, the bacterial pellet resuspended in 36 ml TE buffer and transferred to SS34 tubes. The suspension is centrifuged for 5 min at 0° C. with 5000 rpm. The pellet is resuspended in 7.5 ml 25% sucrose/50 mM Tris.HCl, pH 7.5, treated with 0.75 ml of freshly prepared lysozyme (10 mg/ml in 250 mM Tris.HCl, pH 7.5) and incubated for 5 min on ice. 3.0 ml 0.25 M EDTA, pH 8.0, and, after 5 min, 12 ml Triton-Sol (0.1% Triton X-100® [Sigma], 60 mM EDTA, 50 mM Tris.HCl, pH 8.0) are added and the incubation continued for 1 h at 0° C. The mixture is centrifuged in a SS34 centrifuge at 18,000 rpm for 50 min. The supernatant is carefully poured in a measuring cylinder and the volume adjusted to 30 ml with TE buffer. 30 g CsCl and 2.58 ml ethidium bromide (10 mg/ml) are added and the mixture centrifuged for 16 h at 20° C. with 48,000 rpm in a VTi 50 centrifuge. The lower band consisting of supercoiled DNA is collected, extracted 5 times with isopropanol saturated with aqueous CsCl, and diluted with TE buffer to remove turbidity. The DNA is precipitated with ethanol at −20° C., then purified once more in a CsCl gradient as above.

EXAMPLE 7

Tests Proving that the Selected Clone Codes for the 78 kDa Interferon-induced Protein 7.1 Northern Blot:

Total RNA from IFN-induced human embryonic foreskin cells isolated according to Examples 4.1 and 4.2 and total RNA from corresponding cells not induced with interferon are denatured with 1 M glyoxal in 50% (v/v) dimethyl sulfoxide and 10 mM sodium phosphate buffer, pH 7.0, electrophoresed on 1.1% agarose gel and transferred to nitrocellulose using 3 M NaCl/0.3 M trisodium citrate essentially as described by P. S. Thomas [Proc. Natl. Acad. Sci. USA 77, 5201–5205 (1980)]. The nitrocellulose filters are baked for 2 h at 80° C. under vacuum, prehybridized in a buffer containing 5×SSC/50% formamide for 3 h at 42° C., then hybridized for 20 h at 42° C. in the same buffer containing dextran sulfate 500 and $0.5-1.0 \times 10^6$ cpm/ml of DNA from clone B1,1 (Example 6) labelled with $\gamma$-$^{32}$P-dATP and polynucleotide kinase as described above. The filters are washed four times 5 min at 20° C. in 2×SSC/0.1% SDS and twice 20 min at 50° C. in 0.1×SSC/0.1% SDS. The dry filters are exposed to Kodak XAR film with a Cawo intensifying screen for 6 days at −70° C.

The DNA of clone B1,1 hybridizes to an RNA of approximately 23S corresponding in size to the expected mRNA coding for the 78 kDA interferon-induced protein. This mRNA is detected only in interferon-induced cells.

7.2 Hybrid Selected Translation

10 µg plasmid DNA of clone B1,1 (Example 6) in 20 µl H$_2$O are heated to 100° C. for 10 min, cooled quickly in ice, treated with 20 µl 1 M NaOH and incubated at room temperature for 20 min. The DNA sample is neutralized with 20 µl of a solution of 1M NaCl, 0.3 M trisodium citrate, 0.5 M Tris.HCl and 1M HCl, then spotted on a nitrocellulose filter (3×6 mm, Millipore HAWP). The filter is dried at 20° C. and baked for 2 h at 80° C. in a vacuum oven. The filter is placed in a siliconized 1.5 ml Eppendorf tube, treated with 1 ml H$_2$O, heated in a boiling water bath for 1 min and cooled in ice. The water is removed and 50 µl of a solution containing 100 µg total mRNA from IFN-induced cells (Example 4.2) in 0.9 M NaCl, 0.2% SDS, 1 mM EDTA and 20 mM PIPES (1,4-piperazine-diethanesulfonic acid, pH 6.4) added. The filter is incubated for 6 h at 37° C. with constant agitation, then washed five times in 1 ml washing buffer consisting of 50% formamide, 20 mM NaCl, 8 mM trisodium citrate, 1 mM EDTA and 0.5% SDS for 15 min at 37° C. The hybridized mRNA is eluted with 100 µl 1 mM EDTA containing 10 µg tRNA in a boiling water bath for 1 min. The solution is frozen by plunging into dry ice, thawed on ice, and the filter removed. 7 µl 3 M sodium acetate are added and the mixture extracted with phenol/chloroform/isoamyl alcohol (1:1:0.04 v/v). 250 µl ethanol are added to the aqueous phase to precipitate the mRNA.

The eluted mRNA is translated in reticulocyte lysate (Amersham International No. N90) according to the instructions of the manufacturer. An aliquot of the proteins synthesized in vitro is separated by polyacrylamide gel electrophoresis, and radioactive proteins (from $^{35}$S-methionine in the translation system) detected by fluorography. Another aliquot of proteins is immunoprecipitated with monoclonal antibodies specific for the 78 kDa protein of Example 13. The immunoprecipitate is also separated by polyacrylamide gel electrophoresis and detected by fluorography.

The mRNA selected by the hybridization with DNA from clone B1,1 directs the synthesis of a protein with the same apparent molecular weight and the same antigenic properties as the 78 kDa protein isolated from IFN-induced Namalwa cells (Example 2).

EXAMPLE 8

Subcloning of Plasmid DNA into an M13 Vector

The plasmid DNA of clone B1,1 of Example 6 is fragmented with the restriction enzyme PstI (Boehringer-Mannheim) according to the manufacturer's instructions. The insert is isolated and precipitated with ethanol.

Bluescript M13 vector (Stratagene) is cut with PstI. 20 µg vector DNA are dephosphorylated in 50 µl solution containing 8 units calf alcaline intestinal phosphatase, 100 mM glycine, pH 10.5, 1 mM $MgCl_2$ and 1 mM $ZnCl_2$. The vector DNA is isolated and purified by phenol/chloroform extraction.

0.5 µg cDNA of clone B1,1 and 1.5 µg M13 vector DNA are ligated by incubation for 5 h at 23° C. in 20 µl ligation buffer containing 5 units $T_4$ DNA ligase and 0.5 mM ATP. $CaCl_2$ treated E. coli $rec^{A-}$ JM109 are transformed with this DNA solution. The cells are plated on LB plates containing 100 µg/ml ampicillin, 40 µg/ml X-Gal (5-bromo-4-chloro-3-indolyl β-D-galactopyranoside) and 5 mM IPTG (isopropyl β-D-thiogalactopyranoside). The colonies are grown overnight at 37° C., and transformants selected by white color from blue cell plaques containing unchanged M13 vector.

Selected individual colonies are grown in 1 ml of LB medium containing 50 µg/ml ampicillin overnight at 37° C. After centrifugation the supernatant is discarded and the pellet suspended in 100 µl 50 mM glucose, 25 mM Tris.HCl, pH 8.0, and 10 mM EDTA. After 5 min at 22° C., 200 µl 0.2 N NaOH/1% SDS are added, the mixture incubated at 0° C. for 5 min, treated with 150 µl precooled 3 M sodium acetate, pH 4.8, and kept at 0° C. for another 5 min. The mixture is centrifuged in an Eppendorf tube for 1 min. 1 ml ethanol is added to the supernatant, and the mixture, after 2 min at 20° C., centrifuged again for 1 min. The pellet is washed with 80% ethanol and resuspended in 100 µl 300 mM sodium acetate. 300 µl ethanol are added, and the mixture kept at −80° C. for 30 min, then centrifuged. The pellet is washed with 80% ethanol, dried and suspended in 15 µl TE buffer.

2 µl of this DNA suspension are digested with PstI. Another sample of 2 µl is double digested with SacI and HindI. The obtained restriction fragments are analyzed by electrophoresis on 7% polyacrylamide gels in order to determine the orientation of the cDNA insert in the vector.

EXAMPLE 9

Subcloning of Plasmid DNA After Unidirectional Deletions

Plasmids from clones of Example 8 containing the cDNA insert in either direction are isolated using the method described in Example 6 except that the clones are cultured in LB medium containing 100 µg/ml of ampicillin instead of tetracycline, and no chloramphenicol is added.

The plasmid DNA is digested to completion with KpnI and HindIII, then extracted with phenol. 18 µg of this double digested DNA in 300 µl 50 mM Tris.HCl, pH 8, 5 mM $MgCl_2$, 10 µg/ml tRNA, 20 mM 2-mercaptoethanol containing 900 units of exonuclease Exo III are incubated at 23° C. 50 µl aliquots are removed from the reaction mixture every minute up to 6 min, added to a tube with 80 µl 5× concentrated mung bean nuclease buffer and 270 pi water and frozen in dry ice. The aliquots are heated at 68° C. for 15 min, then treated with 9 units of mung bean nuclease in mung bean nuclease buffer for 30 min at 30° C. The reaction is quenched with 400 µl of buffer-equilibrated phenol/chloroform per aliquot, and the DNAs isolated by ethanol precipitation.

These DNAs are re-ligated, and the hybrid vectors obtained used to transform E. coli $Rec^{A-}$ JM109 as described in Example 8. Transformants are grown in LB medium containing 100 µg/ml ampicillin overnight at 37° C. Plasmid DNA is isolated and purified in a CsCl gradient as described in Example 6.

EXAMPLE 10

Determination of the DNA Sequence

The sequence is determined on the DNAs of Example 6 and Example 9 with the $^{20}$-mer oligonucleotide mixture of Example 5 as a primer following standard procedures (dideoxynucleotide method). The partial sequence of formula II is confirmed by upstream and downstream sequencing using a second primer of the formula 5'-CAGCCACCATTCCAAGG-3' (SEQ ID NO.15) and a third primer of the formula 5'-CGCACCTTCTCCTCATACTGG-3' (SEQ ID NO.16) synthesized according to Y. Ike et al. [Nucleic Acid Research 11, 477 (1983)].

In brief, 5 µg of plasmid DNA of Example 6 or 9 are linearized with the restriction enzyme PstI (Boehringer-Mannheim) according to the manufacturer's instructions. The DNA is precipitated with 3 volumes of ethanol, then dissolved in 25 µl TE buffer. 8 µl of this solution and 2 µl TE buffer containing 0.5 nmol/ml of the primer are mixed, placed in a boiling water bath for 3 min, then frozen by plunging into dry ice. 1 µ of 0.1 M Tris.HCl/50 mM $MgCl_2$, pH 7.4, is added and the mixture incubated for 30 min at 42° C. This primer/template mixture is treated with dNTP mix, α-$^{35}$S-dATP, Klenow fragment and the dideoxynucleotides ddATP, ddCTP, ddGTP, ddTTP, respectively, following standard procedures [J. R. Dillon, A. Nasim and E. R. Nestmann, "Recombinant DNA methodology", Wiley 1985, p. 90–94]. The DNA is denatured and loaded immediately onto a sequencing 6% polyacrylamide 7 M urea gel [J. R. Dillon et al., loc. cit., p. 89] and the gel run with 90 nM Tris borate/1 mM EDTA, pH 8.3.

The ATG at position 1 of formula II is most certainly the initiation codon for the protein, since upstream sequences contain termination codons at positions −75 (TGA), −65 (TAA), −57 (TGA) and −41 (TGA).

EXAMPLE 11

Preparation of Hybridoma Cells 11.1 Immunization protocol:

5 µg portions of the purified protein (Example 2) are dissolved in 20 µl of 2 M urea solution containing 0.1% SDS and 50 mM mercaptoethanol. A nitrocellulose piece 5×5 mm containing 5 µg protein is implanted into the peritoneal cavity of a female HR-mouse [obtained from Dr. Biozzi, Institute Curie, Paris, see L. Boumsell & A. Bernard, J. Immunol. Methods 38, 225 (1980)]. Four weeks later 5 µg 78 kDa protein in incomplete Freund's adjuvant containing 50 µg adjuvant peptide (Sigma) are injected intraperitoneally (i.p.), and three bi-weekly booster immunizations with the same sample compositions are given i.p. After four weeks, serum is collected and the antibody titer to the 78 kDa protein determined by the dot-immunoassay of Example 12. Mice with high antibody titer are further immunized by two more bi-weekly injections and a final booster immunization one week later. After three days the spleen is taken for the fusion.

11.2 Cell Fusion:

All fusion experiments are performed according to the procedure of G. Köhler and C. Milstein [Nature 256, 495 (1975)] using the nonsecreting Sp2/0-Ag14 myeloma line [M. Shulman, C. D. Wilde and G. Köhler, Nature 276, 269 (1978)]. $10^8$ spleen cells are mixed with $10^7$ myeloma cells in the presence of 1 ml of 50% polyethylene glycol (PEG 1500, Serva). After washing, the cells are resuspended in 48 ml of standard Dulbecco's minimum essential medium (Gibco No. 0422501). $3 \times 10^6$ normal mouse peritoneal exsudate cells per fusion are added as feeder cells. The cells are distributed into 48×1 ml Costar wells and fed 3 times per week with standard HAT selection medium for 3 to 6 weeks. When the growth of hybridoma cells becomes visible, the supernatants are screened by the dot-immunoassay of Example 12. The hybridoma cells are cloned by limiting dilution in microtiter plates at least once, then passaged through HR mice by i.p. injection. Hybridoma cells are harvested from ascites and cloned once more by limiting dilution. The nine hybridomas selected for further studies are particularly stable and secrete large quantities of immunoglobulin. They are designated 885 S35.8.1, 885 S35.16.11, 885 S56.55.7.12.48, 885 S56.55.7.21.25, 885 S56.55.7.27.5, 885 S56.55.7.27.11, 885 S56.55.13, 885 S56.55.17, and 885 S56.67.15.

EXAMPLE 12

Dot-immunoassay for Antibody Screening

The purified protein of Example 2 is dissolved in 2 M urea, 0.1% SDS and 50 mM mercaptoethanol. The dilutions of the protein are made in TBS containing 10%. inactivated horse serum. The protein is applied in the form of dots (0.2 $\mu$l) onto nitrocellulose (type HAWG from Millipore Corp., Bedford, Mass.). The dilutions of antibodies from mouse serum or hybridoma culture medium are made in TBS containing 10% inactivated horse serum. The dot immunobinding assay, a modified enzyme-linked immunosorbent assay, is carried out using a rabbit anti-mouse IgG peroxidase conjugated second antibody and $H_2O_2$/4-chloro-1-naphthol in TBS as described by M. M. Derer et al. [J. Allergy Clin.Immunol. 74, 85 (1984)].

EXAMPLE 13

Isolation and Purification of Monoclonal Antibodies
13.1 In Vivo Synthesis:
Balb/c mice 8–10 weeks of age (Tierfarm Sisseln, Switzerland) are pretreated intraperitoneally with 0.3 ml pristane (Aldrich). 2–3 weeks later, 2–5×10⁶ cloned hybridoma cells and 0.2 ml pristane are inoculated intraperitoneally. After 8–10 days ascites fluid is collected, centrifuged at 800×g and stored at −20° C.

Defrosted ascites fluid is centrifuged at 50,000×g for 60 min. A fat layer floating on the surface is carefully removed, and the protein concentration is adjusted to a concentration of 10–12 mg/ml. Crude immunoglobulin is precipitated by dropwise addition of 0.9 volume equivalents of saturated ammonium sulphate at 0° C., then dissolved in 20 mM Tris.HCl/50 mM NaCl (pH 7.9) and dialyzed against the same buffer. An immunoglobulin fraction is obtained by DEAE-D52 cellulose (Whatman) chromatography using a buffer gradient system of 20 mM Tris.HCl/25–400 mM NaCl, pH 7.9. The immunoglobulin is again precipitated with ammonium sulphate and dissolved in PBS at a concentration of 10 mg/ml.

SDS polyacrylamide gel electrophoresis demonstrates a purity grade of more than 95 percent for all the monoclonal antibodies.
13.2 In Vitro Synthesis:
A preculture of a cell line of Example 11.2 is obtained by culturing hybridoma cells at physiological temperature (around 37° C.) in RPMI 1640 medium containing 10% FCS to a final cell density of 5×10⁵ to 10⁶ cells per ml. The whole preculture is filled into Bellco culture vessels and adjusted to a total volume of 1500 ml with fresh RPMI 1640 medium/ 10% FCS. The culture is stirred at around 37° C. under 5% $CO_2$ at 30 rpm for two to three days, then diluted to a total volume of 3000 ml with RPMI 1640/10% FCS and stirred for another seven to ten days. After this time 95% of the cells are dead. The culture broth is centrifuged at 1000×g for 20 min at 4° C. The supernatant is filtered through a filter with pore size 0.2 $\mu$m under sterile conditions. Crude immunoglobulin is precipitated by slow dropwise addition of 0.9 volume equivalents of saturated ammonium sulfate at 0° C. This precipitate is purified as described in Example 13.1 and gives monoclonal antibodies with a purity of 95% or more.

EXAMPLE 14

Characterization of Monoclonal Antibodies
14.1 Determination of Class and Subclass of Monoclonal Antibodies:

The class and subclass of monoclonal antibodies produced by cloned hybridoma cells is determined by the known agar-gel immunodiffusion technique of Ouchterlony using class and subclass specific rabbit antibodies (Bionetics). The results are confirmed by an enzyme immunoassay (ELISA) in the following way: Microtiter plates are coated with 1 $\mu$g per well of a rabbit immunoglobulin preparation of a class- or subclass-specific serum (Bionetics) in 50 $\mu$l of PBS. Free binding capacity of the plate is saturated with a buffer of 1% bovine serum albumin in PBS containing 0.2% $NaN_3$ (w/v), pH 7.4. 100 $\mu$l probes containing monoclonal antibodies are incubated in the wells at 37° C. for 1 h. The plates are washed with PBS, then incubated at 37° C. for 1 h with a phosphatase conjugated rabbit immunoglobulin preparation of the same specificity as used for coating the plates. The fixed enzyme is developed by incubating (37° C., 30 min) with a solution of the enzyme substrate p-nitrophenyl phosphate (1 mg/ml in diethanolamine buffer 10% containing 0.5 mM $MgCl_2$ and 0.02% (w/v) $NaN_3$, pH 9.8) and measuring the optical density at 405 nm. The monoclonal antibodies 885 S35.8.1, 885 S35.16.11, 885 S56.55.7.12.48, 885 S56.55.7.21.25, 885 S56.55.7.27.5, 885 S56.55.7.27.11, 885 S56.55.13, 885 S56.55.17, and 885 S56.67.15. all belong to the class $IgG_1$.
14.2 Selectivity Towards Human 78 kDA Protein:

Mouse A2G embryonic diploid cells, rat embryonic diploid cells, hamster embryonic diploid cells, horse kidney diploid cells and cells of the dermis cell line NBL-6, ATCC No. CCL57, calf kidney diploid cells, cat embryonic lung diploid cells, monkey cells of the Vero cell line ATCC No. CCL81, rabbit embryonic cells, sheep choroid plexus cells, and pig kidney diploid cells and cells of the kidney cell line PK-15, ATCC No. CCL33 are incubated with recombinant interferon α/B–D hybrid as described for human cells in Example 1.2 and 4.1 (M. A. Horisberger & K. de Staritzky, J. gen. Virol. (1987), Vol. 68). In the cells of all of these species at least one protein related to the human 78 kDa protein is detected. These antigenically related proteins are identified with a polyclonal antibody serum obtained from mice immunized with human 78 kDA protein according to Example 11.1. However, the monoclonal antibodies 885 S35.8.1, 885 S56.55.13 and 885 S56.67.15 bind only to human 78 kDa protein and not to the related proteins of the species mentioned when tested in the immunofluorescence test of Example 17, the immunoprecipitation test of Example 18, or in a Western blot. For the Western blot, the proteins are separated by SDS polyacrylamide gel electrophoresis and transferred to nitrocellulose, then tested as described for the immunodot assay of Example 16.

EXAMPLE 15

Enzyme-immunoassay (ELISA)
15.1 Labelling of Monoclonal Antibody 885 S35.8.1 With Alkaline Phosphatase:

1.4 mg of monoclonal antibody 885 S35.8.1 in 1.4 ml of PBS are coupled for 2 h with a solution containing 5 mg of alkaline phosphatase (Sigma P6774, type VII-T) according to the standard method of Voller et al. [Bull. World Health Organ. 53, 55 (1976)] using glutaraldehyde (0.2% v/v). The conjugate is transferred into 5 ml of Tris buffer 0.05 M, pH 8.0, containing 1 mM $MgCl_2$, 1% BSA and 0.02% $NaN_3$. The solution is kept in the dark at 4° C.

15.2 Assay Procedure:

Polypropylene Microtitre Plates (Dynatech Labs. Inc.) are coated over a period of 2 h at 37° C. and overnight at 4° C. with 150 µl of a solution of the monoclonal antibody 885 S56.55.13 (10 µg/ml) in a buffer pH 8.6 (carbonate-buffered 0.9% saline containing 0.02% sodium azide). The plates are washed five times with PBS, and protein-reactive sites still present are saturated by incubation for 1 h at 37° C. with 250 µl of a buffer pH 7.4 (0.2% gelatine and 0.2% $NaN_3$ in PBS). Plates coated in this manner can be kept at 4° C. in this buffer for a few days.

50 µl of a dilution series of a test solution or a standard solution containing the 78 kDa protein, 50 µl of buffer pH 7.4 and 50 µl of a solution of the phosphatase-labelled antibody 885 S35.8.1 (Example 15.1) diluted 1:100 with buffer pH 7.4 are mixed and incubated in the wells of the microtiter plates for 2 h at 37° C. and for 30 minutes at 4° C. The plates are washed five times with PBS, then incubated for 30 min at 37° C. with 150 µl of a solution of p-nitrophenyl phosphate (1 mg/ml in 10% diethanolamine buffer, 0.5 mM $MgCl_2$, pH 9.8). By measuring the optical density at 405 nm, the amount of released p-nitrophenol is determined, which is proportional to the amount of the bound enzyme phosphatase and hence proportional to the amount of the 78 kDa protein in the test solution.

Similar results are obtained, when the microtiter plates are coated with monoclonal antibody 885 S35.8.1 or 885 S56.67.15 and phosphatase-coupled monoclonal antibody 885 S56.55.13 is used as second antibody.

15.3 Test Kit for ELISA:

A test kit for the assay described in Example 15.2 contains

--- polypropylene microtiter plates,
  20 ml of monoclonal antibody 885 S56.55.13 (10 µg/ml) in carbonate-buffered saline (0.9% NaCl, 0.42% $NaHCO_3$, 0.0072% $Na_2CO_3$, 0.02% $NaN_3$)
  1 ml of alkaline phosphatase-coupled monoclonal antibody 885 S35.8.1 (Example 15.1, 0.3 mg antibody per ml) in Tris buffer (0.05 M, 1 mM $MgCl_2$, 1% BSA, 0.02% $NaN_3$, pH 8.0)
  2 ml standard solution containing 5 µg 78 kDa protein
300 ml PBS
300 ml buffer pH 7.4 (0.2% gelatine and 0.2% $NaN_3$ in PBS)
  50 ml of p-nitrophenyl phosphate (1 mg/ml) in diethanolamine buffer (10%, 0.5 mM $MgCl_2$, 0.02% $NaN_3$, adjusted to pH 8.9 with HCl)
calibration curve
colour intensity scale
instruction manual

---

EXAMPLE 16

Immunodot Assay 16.1 Assay Procedure:

A dilution series of the solution to be tested for the presence of the 78 kDa protein and of a standard solution are prepared in TBS containing 10% inactivated horse serum. The dilutions are applied in the form of dots (0.2 µl) onto nitrocellulose (type HAWG, Millipore Corp., Bredford, Mass.). The excess protein-binding capacity of the nitrocellulose is blocked by incubating the nitrocellulose for 2 h at 37° C. in TBS containing 10% horse serum. The nitrocellulose is cut into suitable strips, then incubated with solutions of the monoclonal antibody 885 S56.55.13 or 885 S35.8.1 (2 µg/ml and 10 µg/ml) in TBS for 2 h at room temperature. The strips are washed five times in TBS and further incubated for 2 h in a 10,000-fold dilution of a rabbit anti-mouse IgG peroxidase conjugated second antibody, washed five times in TBS, then developed in a freshly mixed peroxidase substrate solution consisting of 0.6 volumes of 4-chloro-1-naphthol (3 mg/ml in methanol), 10 volumes of TBS and 0.004 volumes of 30% hydrogen peroxide for 15 min at room temperature. If desired the spots can be scanned with a reflectance densitometer at 600 nm (CAMAG, Muttenz, Switzerland).

16.2 Test Kit for Immunodot Assay:

A test kit for the assay described in Example 16.1 contains

---

Nitrocellulose sheets
  20 ml of monoclonal antibody 885 S56.55.13 (10 µg/ml) in TBS containing 10% horse serum
  1 ml of a 1:100 dilution of rabbit anti-mouse IgG conjugated to horseradish peroxidase in TBS containing 10% horse serum
  2 ml standard solution containing 5 µg 78 kDa protein
300 ml TBS
300 ml TBS containing 10% horse serum
  10 ml 4-chloro-1-naphthol (3 mg/ml in methanol)
  10 ml 30% hydrogen peroxide
instruction manual

---

EXAMPLE 17

Immunofluorescence Test

Cells to be tested for the presence of the protein of the invention are grown on plastic coverslips. Alternatively, freshly isolated cells from human blood, e.g. lymphocytes or monocytes, are attached by cytospin centrifugation to glass slides pretreated with poly-D-lysine.

The cells are washed with PBS, fixed at 20° C. for 10 min with 3% aqueous paraformaldehyde, permeabilized for 5 min with 0.5% Triton X-100®, washed once more with PBS, and incubated with a solution of the monoclonal antibody 885 S56.55.13 (10 µg/ml) in PBS for 60 min at 37° C. The cells are washed with PBS, treated with a solution of fluorescein-conjugated rabbit anti-mouse IgG (DAKO, diluted 1:40 in PBS containing 5%, horse serum), washed with PBS, and mounted as described by Johnson et al. [J. Immunol. Methods 43, 349 (1981)]. UV fluorescence microscopy reveals the presence of the protein of the invention by a bright fluorescence in the cytoplasm of the cells.

EXAMPLE 18

Immunoprecipitation Test for Cells Induced With Interferon

Cells grown in culture or cells freshly isolated from human blood are mounted on plastic or glass plates as described in Example 17. The cells are treated with a solution of recombinant interferon $5_1$ (α/B type) at a concentration of 5000 international units per ml for 4 h at 37° C., then incubated for 30 min at 37° C. with 50 µCi per ml of $^{35}$S-methionine in Hank's balanced salt solution containing sodium bicarbonate, buffered with 20 mM N-2- hydroxyethylpiperazine-N'-2-ethanesulfonic acid (HEPES, pH 7.4). The cells are washed with PBS, scraped off the plates, collected by centrifugation, suspended in hypotonic buffer consisting of 5 mM Tris pH 7.4, 1.5 mM KCl and 2.5 mM MgCl2 for 5 min, and collected again by centrifugation. The cells are lysed with the hypotonic buffer containing 1% Triton X-100® and 1% deoxycholate for 5 min at 4° C., then centrifuged at 12,000 rpm for 5 min. Sodium dodecyl sulfate is added to the supernatant at a final concentration of 0.5%. 6 µl of this solution and 20 µl of a buffer consisting of 10 mM Tris.HCl, pH 7.4, and 50 mM NaCl (saturated with phenylmethylsulfonyl fluoride) are mixed and recentrifuged at 12,000 rpm for 5 min. 20 µl of the supernatant and 1 µl of a solution of the monoclonal antibody 885 S56.55.13 (40 µg/ml) in PBS containing 0.5%. BSA are incubated for 3 h at 4° C., then mixed with 20 µl of a 50% (v/v) suspension of Protein A-Sepha-rose®. The sepharose beads are washed with 500 µl of a buffer consisting of 10 mM Tris pH 7.4, 50 mM NaCl, 1 M sucrose, 0.5% deoxycholate and 0.5% Triton X-100®, and the antigen/antibody complex eluted with 30 µl of sample buffer [U. K. Laemmli & M. Favre, J. Mol. Biol. 80, 575 (1973)]. The eluate is analyzed by one-dimensional SDS gel electrophoresis on 12% polyacrylamide gels in the usual way. The presence of the protein of the invention at an apparent molecular weight of 78 kDa is revealed by fluorography.

EXAMPLE 19

Surveillance of Interferon Therapy in Humans

Blood samples are taken from patients receiving $10^7$ international units of recombinant human interferon alpha ($\beta_2$) subcutaneously 24 h and 48 h after injection. The lymphocytes are purified by centrifugation on Ficoll 400 (Pharmacia) density gradient. $4.5 \times 10^6$ lymphocytes are suspended in 400 µl H$_2$O, then precipitated with 800 µl ethanol. The pellet is dissolved in dissociation buffer and separated by one-dimensional SDS polyacrylamide gel electrophoresis. The proteins are transferred onto nitrocellulose and the 78 kDa protein detected and quantified as described in Example 16.

Compared to patients before interferon treatment and to healthy humans, the level of the 78 kDa protein is increased fivefold at 24 h and 4.8 h after s.c. interferon $\alpha_2$ injection.

EXAMPLE 20

Pharmaceutical Preparation for Parenteral Application

200 µg of the 78 kDa protein are dissolved in 3 ml of 5N human serum albumin. The resulting solution is passed through a bacteriological filter and the filtered solution subdivided under aseptic conditions into 10 vials. The vials are preferably stored in the cold, for example at −20° C.

What is claimed is:

1. A substantially pure protein, wherein said protein is present in Namalwa cells treated with interferon α or β,
   has a molecular weight of approximately 78 kDa as determined by sodium dodecyl sulfate polyacrylamide electrophoresis (SDS-PAGE),
   has an isoelectric point of approximately 6.3, and comprises (SEQ ID NO:1).

2. The protein of claim 1, that comprises the sequence of SEQ ID NO:2.

3. The protein of claim 1, wherein said Namalwa cells are treated with a recombinant interferon α/β, αD, α/F or interferon α/B–D hybrids.

4. A protein of claim 1, 2 or 3, characterized by the following range of amino acid composition: Asx 54–60, Glx 91–101, Ser 37–41, Thr 30–34, Gly 41–46, Ala 45–50, Arg 36–40, Pro 24–28, Val 38–42, Met 17–19, Ile 41–46, Leu 64–72, Trp 0–3, Phe 24–27, Cys 5–7, Lys 45–50, His 12–14, and Tyr 11–13.

* * * * *